United States Patent
Cui et al.

(10) Patent No.: US 8,411,282 B2
(45) Date of Patent: *Apr. 2, 2013

(54) ON-CHIP PHASE MICROSCOPE/BEAM PROFILER BASED ON DIFFERENTIAL INTERFERENCE CONTRAST AND/OR SURFACE PLASMON ASSISTED INTERFERENCE

(75) Inventors: Xiquan Cui, Pasadena, CA (US);
Changhuei Yang, Pasadena, CA (US);
Axel Scherer, Woodstock, VT (US);
Demetri Psaltis, Preverenges (CH); Xin Heng, Hercules, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/157,245

(22) Filed: Jun. 9, 2011

(65) Prior Publication Data
US 2012/0026509 A1 Feb. 2, 2012

Related U.S. Application Data

(60) Continuation of application No. 12/823,201, filed on Jun. 25, 2010, now Pat. No. 7,982,883, which is a division of application No. 11/743,581, filed on May 2, 2007, now Pat. No. 7,768,654.

(60) Provisional application No. 60/796,997, filed on May 2, 2006, provisional application No. 60/796,996, filed on May 2, 2006.

(51) Int. Cl.
*G01B 9/02* (2006.01)

(52) U.S. Cl. ...................................................... 356/521

(58) Field of Classification Search .................. 356/521, 356/436, 516
See application file for complete search history.

(56) References Cited

U.S. PATENT DOCUMENTS

| | | | |
|---|---|---|---|
| 4,981,362 A | | 1/1991 | DeJong et al. |
| 5,196,350 A | * | 3/1993 | Backman et al. ............. 436/501 |
| 5,362,653 A | | 11/1994 | Carr et al. |
| 5,426,505 A | | 6/1995 | Geiser et al. |
| 5,973,316 A | | 10/1999 | Ebbesen et al. |
| 6,499,499 B2 | | 12/2002 | Dantsker et al. |
| 6,858,436 B2 | | 2/2005 | Zenhausern et al. |
| 7,045,781 B2 | | 5/2006 | Adamec et al. |

(Continued)

FOREIGN PATENT DOCUMENTS

| | | |
|---|---|---|
| EP | 1 371 965 | 12/2003 |
| JP | 2003-207454 A | 7/2003 |

(Continued)

OTHER PUBLICATIONS

Aigouy, L., et al., "Near-field analysis of surface waves launched at nanoslit apertures," Physical Review Letters, vol. 98, pp. 153902-1-153902-4 (Apr. 2007).

(Continued)

*Primary Examiner* — Tarifur Chowdhury
*Assistant Examiner* — Jonathan Hansen
(74) *Attorney, Agent, or Firm* — Sheila Martinez-Lemke; Weaver Austin Villeneuve & Sampson LLP

(57) ABSTRACT

A differential interference contrast (DIC) determination device and method utilizes an illumination source, a layer having a pair of two apertures that receive illumination from the illumination source, and a photodetector to receive Young's interference from the illumination passing through the pair of two apertures. In addition, a surface wave assisted optofluidic microscope and method utilize an illumination source, a fluid channel having a layer with at least one aperture as a surface, and a photodetector that receives a signal based on the illumination passing through the aperture. The layer is corrugated (e.g., via fabrication) and parameters of the corrugation optimize the signal received on the photodetector.

30 Claims, 15 Drawing Sheets

U.S. PATENT DOCUMENTS

| | | | |
|---|---|---|---|
| 7,250,598 B2 | 7/2007 | Hollingsworth et al. | |
| 7,271,885 B2 | 9/2007 | Schermer | |
| 7,283,229 B2 | 10/2007 | Noguchi et al. | |
| 7,751,048 B2 | 7/2010 | Yang et al. | |
| 7,768,654 B2 | 8/2010 | Cui et al. | |
| 7,773,227 B2 | 8/2010 | Yang et al. | |
| 7,982,883 B2* | 7/2011 | Cui et al. | 356/521 |
| 8,189,204 B2 | 5/2012 | Cui et al. | |
| 2003/0142291 A1 | 7/2003 | Padmanabhan et al. | |
| 2003/0174992 A1 | 9/2003 | Levene et al. | |
| 2003/0203502 A1 | 10/2003 | Zenhausern et al. | |
| 2004/0156610 A1 | 8/2004 | Charlton et al. | |
| 2004/0175734 A1 | 9/2004 | Stahler et al. | |
| 2004/0190116 A1* | 9/2004 | Lezec et al. | 359/298 |
| 2004/0224380 A1 | 11/2004 | Chou et al. | |
| 2005/0271548 A1* | 12/2005 | Yang et al. | 422/82.05 |
| 2006/0003145 A1 | 1/2006 | Hansen et al. | |
| 2006/0013031 A1 | 1/2006 | Ravkin et al. | |
| 2007/0172745 A1 | 7/2007 | Smith | |
| 2007/0207061 A1 | 9/2007 | Yang et al. | |
| 2007/0258096 A1 | 11/2007 | Cui et al. | |
| 2009/0225319 A1 | 9/2009 | Lee et al. | |
| 2009/0276188 A1 | 11/2009 | Cui et al. | |
| 2010/0195873 A1 | 8/2010 | Cui et al. | |
| 2010/0290049 A1 | 11/2010 | Yang et al. | |
| 2010/0296094 A1 | 11/2010 | Yang et al. | |
| 2010/0309457 A1 | 12/2010 | Cui et al. | |
| 2011/0063623 A1 | 3/2011 | Cui et al. | |
| 2011/0075254 A1* | 3/2011 | Cui et al. | 359/370 |
| 2011/0170105 A1 | 7/2011 | Cui et al. | |
| 2011/0181884 A1 | 7/2011 | Cui et al. | |
| 2012/0250027 A1 | 10/2012 | Zheng et al. | |

FOREIGN PATENT DOCUMENTS

| | | |
|---|---|---|
| JP | 2003-524779 A | 8/2003 |
| JP | 2004-505272 A | 2/2004 |
| WO | WO 02/10713 A2 | 2/2002 |
| WO | WO 2004/038484 A2 | 5/2004 |
| WO | WO 2005/121749 | 12/2005 |
| WO | WO 2008/112416 | 9/2008 |

OTHER PUBLICATIONS

Arnison, M.R., et al., "Linear phase imaging using differential interference contrast microscopy," Journal of Microscopy, vol. 214, Pt. 1, pp. 7-12 (Apr. 2004).

Bouwkamp, C.J., "Diffraction theory," Reports on Progress in Physics XVIII, pp. 35-100 (1954).

Chen, L., et al. "Role of radiation and surface plasmon polaritons in the optical interactions between a nano-slit and a nano-groove on a metal surface," Optics Express, vol. 14, pp. 12629-12636 (2006).

Cui, Xiquan, et al., "Portable optical microscope-on-a-chip," P{roc. of SPIE, vol. 6095, pp. 609509-1-609509-8 (Jan. 2006).

Cui, Xiquan, et al., "Quantitative differential interference contrast microscopy based on structured-aperture interference," Applied Physics Letters, vol. 93, pp. 091113-1-091113-3 (2008).

Cui, Xiquan, et al., "Slanted hole array beam profiler (SHArP)—a high-resolution portable beam profiler based on a linear aperture array," Optics Letters, vol. 31, No. 21, pp. 3161-3163 (Nov. 2006).

Doyle, Patrick S., et al., "Self-assembled magnetic matrices for DNA separation chips," Science, vol. 295, No. 5563, p. 2237 (Mar. 2002).

Drezet, Aurelien, et al., "Miniature plasmonic wave plates," Physical Review Letters, vol. 101, pp. 43902-1-43902-4 (Jul. 2008).

Dunn, et al., "Introduction to Confocal Microscopy," available from MicroscopyU at http://www.microscopyu.com/articles/confocal (2007).

Ebbesen, T.W., et al., "Extraordinary optical transmission through sub-wavelength hole arrays," Nature, vol. 391 (6668), pp. 667-669 (Feb. 1998).

Fu, Anne Y., et al., "A microfabricated fluorescence-activated cell sorter," Nature Biotechnology, vol. 17, pp. 1109-1111 (Nov. 1999).

Garcia De Abajo, F. J., "Light transmission through a single cylindrical hole in a metallic film," Optics Express, vol. 10, No. 25, pp. 1475-1484 (2002).

Gay, G., et al., "The optical response of nanostructured surfaces and the composite diffracted evanescent wave model," Nature Physics, vol. 2, pp. 262-267 (Mar. 2006).

Gbur, Greg, et al., "Achieving superresolution in near-field optical data readout systems using surface plasmons," Applied Physics Letters, vol. 87, Issue 19, pp. 191109-1-191109-3 (2005).

Heng, Xin, et al., "Characterization of light collection through a subwavelength aperture from a point source," Optics Express, vol. 14, pp. 10410-10425 (2006).

Heng, Xin, et al., "Optofluidic Microscope, a miniature microscope on a chip," 9th International Conference on Miniaturized Systems for Chemistry and Life Sciences (μTAS) (2005).

Heng, Xin, et al., "Optofluidic Microscopy—a method for implementing a high resolution optical microscope on a chip," Lab Chip, vol. 6, pp. 1274-1276 (2006).

Lalanne, P., and Hugonin, J. P., "Interaction between optical nano-objects at metallo-dielectric interfaces," Nature Physics, vol. 2, pp. 551-556 (Aug. 2006).

Laux, Eric, et al., "Plasmonic photon sorters for spectral and polarimetric imaging," Nature Photonics, vol. 2, pp. 161-164 (Feb. 2008).

Leen, Brian J., et al.,"Improved focused ion beam fabrication of near-field apertures using a silicon nitride membrane," Optics Letters, vol. 33, No. 23, pp. 2827-2829 (2008).

Lezec, Henri J., et al., "Beaming Light from a Subwavelength Aperture," Science, vol. 297, No. 5582, pp. 820-822 (2002).

Lezec, Henri J., and Thio, Tineke, "Diffracted evanescent wave model for enhanced and suppressed optical transmission through subwavelength hole arrays," Optics Express, vol. 12, No. 16, pp. 3629-3651 (Aug. 2004).

Liu, Haitao, and Lalanne, Philippe, "Microscopic theory of the extraordinary optical transmission," Nature, vol. 452, pp. 728-731 (Apr. 2008).

Liu, Shaorong, "A microfabricated hybrid device for DNA sequencing," Electrophoresis 2003, vol. 24(21), pp. 3755-3761 (2003).

Minakawa, Kyosuke, et al.,"Microchamber Device Equipped with Complementary Metal Oxide Semiconductor Optical Polarization Analyzer Chip for Micro Total Analysis System," Jpn. J. Appl. Phys., vol. 48, pp. 04C192-1-04c192-5 (2009).

Murphy, et al., "Differential Interference Contrast (DIC)," available from Nikon MicrocopyU at http://www.microscopyu.com/articles/dic/dicindex.html (2007).

Ng, Ren, et al., "Light field photography with a hand-held plenoptic camera," Stanford Tech Report CSTR Feb. 2005, vol. 2, pp. 1-11 (2005).

Pacifici, Dominico, et al., "Quantitative determination of optical transmission through subwavelength slit arrays in Ag films: Role of surface wave interference and local coupling between adjacent slits," Physical Review B, vol. 77, pp. 115411-1-115411-5 (2008).

Pacifici, Dominico, et al., "All-optical modulation by plasmonic excitation of CdSe quantum dots," Nature photonics, vol. 1, pp. 402-406 (Jul. 2007).

Pacifici, Dominico, et al., "Universal optical transmission features in periodic and quasiperiodic hole arrays," Optics Express, vol. 16, No. 12, pp. 9222-9238 (Jun. 2008).

Schouten, H. F., et al., "Plasmon-assisted two-slit transmission: Young's experiment revisited," Physical Review Letters, vol. 94, pp. 053901-1-053901-4 (Feb. 2005).

Schwiegerling, Jim, and Neal, Daniel,"Historical development of the Shack-Hartmann wavefront sensor," in Robert Shannon and Roland Shack: Legends in Applied Optics, edited by J. E. Harvey and R. B. Hooker _SPIE, Bellingham, WA, pp. 132-139 (2005).

Shi, Xiaolei, et al., "Ultrahigh light transmission through a C-shaped nanoaperture," Optics letters, vol. 28, No. 15, pp. 1320-1322 (Aug. 2003).

Tegenfeldt, Jonas O., et al., "Micro- and nanofluidics for DNA analysis," Analytical and Bioanalytical Chemistry, 378(7), pp. 1678-1692 (Mar. 2004).

Tegenfeldt, Jonas O., et al., "Near-field Scanner for Moving Molecules," Physical review letters, 86(7), vol. 86, No. 7, pp. 1378-1381 (Feb. 2001).

Thio, Tineke, et al., "Enhanced light transmission through a single subwavelength aperture," Opt. Lett., vol. 26, No. 24 pp. 1972-1974 (Dec. 2001).

Thio, Tineke, et al., "Giant optical transmission of sub-wavelength apertures: physics and applications," Nanotechnology, vol. 13, pp. 429-432 (2002).

Tokeshi, Manabu, et al., "Chemical processing on microchips for analysis, synthesis, and bioassay," Electrophoresis, vol. 24, No. 21, pp. 3583-3594 (2003).

Trau, Dieter, et al., "Genotyping on a complementary metal oxide semiconductor silicon polymerase chain reaction chip with integrated DNA microarray," Analytical Chemistry, vol. 74, No. 13, pp. 3168-3173 (2002).

Ung, Bora, and Sheng, Yunlong, "Optical surface waves over metallo-dielectric nanostructures: Sommerfeld integrals revisited," Optics Express, vol. 16, No. 12, pp. 9073-9086 (Jun. 2008).

Yu, Nanfang, et al., "Semiconductor lasers with integrated plasmonic polarizers," Applied Physics Letters, vol. 94, pp. 151101-1-151101-3 (2009).

Zheng, Guoan, et al., "Surface-wave-enabled darkfield aperture: A method for suppressing background during weak signal detection," Proc Natl Acad Sci U S A, vol. 107, No. 20, pp. 9043-9048 (May 2010).

Wikipedia, "Surface Plasmon," last modified Apr. 4, 2010.

"Differential interference contrast microscopy," Wikipedia, last modified Feb. 10, 2009, downloaded from the Internet at http://en.wikipedia.org/wiki/Differential interference contrast microscopy on Mar. 31, 2009, 4pp.

Adams, Mark L. et al., "Microfluidic Integration on detector arrays for absorption and fluorescence micro-spectrometers," *Sensors and Actuators A*, vol. 104, pp. 25-31 (2003).

Beebe, David J., et al., "Physics and Applications of Microfluidics in Biology," *Annu. Rev. Biomed., Eng.*, vol. 4, pp. 261-286 (2002).

Bethe, H.A., "Theory of Diffraction by Small Holes," *The Physical Review*, vol. 66, Nos. 7-8, pp. 163-182 (1944).

Biddiss, Elaine, et al., "Heterogeneous Surface Charge Enhanced Micromixing for Electrokinetic Flows," *Anal. Chem.*, vol. 76, pp. 3208-3213 (2004).

Boppart, S. A., et al., "Forward-imaging instruments for optical coherence tomography," *Optics Letters*, vol. 22, pp. 1618-1620 (1997).

Cao, Jinhua, et al., "Brownian Particle Distribution in Tube Flows," *Proceedings of IMECE04*, vol. 260, pp. 243-252 (2004).

Cheng, Ya, et al., "Microfluidic laser embedded in glass by three-dimensional femtosecond laser microprocessing," *Optics Letters*, vol. 29, No. 17, pp. 2007-2009 (2004).

Chronis, Nikolas, et al., "Total internal reflection-based biochip utilizing a polymer-filled cavity with a micromirror sidewall," *Miniaturisation for Chemistry, Biology & Bioengineering, Lab Chip*, vol. 4, pp. 125-130 (2004).

Courjon, Daniel, "Near-field Microscopy and near-field optics," *Imperial College Press*, 317 pages. (2003).

Cui, X. et al., "Portable Optical microscope-on-a-chip," *Photonics West*, San Jose, CA, Jan. 2006, 8 pages.

Cui, Xiquan, et al., "Quantitative differential interference contrast microscopy based on structured-aperture interference," *Applied Physics Letters*, vol. 93, pp. 091113-1 —091113-3 (2008).

Dahan, M., et al., "Time-gated biological imaging by use of colloidal quantum dots," *Optics Letters*, vol. 26, No. 11, pp. 825-827 (2001).

De Fornel, F., "Evanescent waves from Newtonian optics and Atomic optics," *Springer Series in Optical Sciences*, 270 pp (2001).

Fowles, G. R., Introduction to Modern Optics, *Dover Publications, Second Ed.*, New York, pp. 57-61 (1989).

Heng, Xin, et al., "Optofluidic Microscopy," Proceedings of the ICMM 2005 3rd International Conference on Microchannels and Minichannels, pp. 1-6 (2005).

Heng, Xin, "OptoFluidic Microscopy (OFM)" *Biophotonics Group, Caltech, DARPA optofluidic center retreat*, Apr. 1, 2005, 9pp.

Lay, Christophe, et al., "Enhanced microfiltration devices configured with hydrodynamic trapping and a rain drop bypass filtering architecture for microbial cells detection," *Lab on a Chip* 2008, 8:830-833; published as Advanced Article on Apr. 1, 2008 at http://pubs.rsc.org I DOI:10.1039/b800015h, 4 pp.

Lee, Lap Man, et al., "The Application of On-Chip Optofluidic Microscopy for Imaging *Giardia lamblia* Trophozoites and Cysts," *Biomed Microdevices*, Springer DOI 10.1007/s10544-009-9312-X (2009) 11:951-958.

Nott, Prabhu R.,, et al., "Pressure-driven flow of suspensions: simulation and theory," (1994), *J. Fluid Mech.*, vol. 275, pp. 157-199.

Nozokido, Tatsuo, et al., "Scanning Near-Field Millimeter-Wave Microscopy Using a Metal Slit as a Scanning Probe," *IEEE Transactions on Microwave Theory and Techniques*, vol. 49, No. 3, 491-99 (2001).

Platt, B. C. and Shack, R., History and Principles of Shack-Hartmann Wavefront Sensing, *Journal of Refractive Surgery*, vol. 17, pp. S573-S577.

Popescu, G., et al., "Optical measurement of cell membrane tension," *Physical Review Letters* 97: 4 pp (2006).

Probstein, R. F., "Physicochemical Hydrodynamics," Wiley, *2nd Edition* pp. 109-116, 123, 190-197, and 309-310 (2003).

Psaltis, Demetri, et al., "Developing optofluidic technology through the fusion of microfluidics and optics," *Nature*, vol. 442:6 pp (2006).

Rappaz, B., et al., "Measurement of the integral refractive index and dynamic cell morphometry of living cells with digital holographic microscopy," *OPTICS EXPRESS*, 13(3):9361-9373 (2005).

Rust, M. J., et al., "Sub-diffraction-limit imaging by stochastic optical reconstruction microscopy (Storm)," *Nature Methods*, vol. 3, pp. 793-795 (2006).

Segre, G., et al., "Behavior of macroscopic rigid spheres in Poiseuille flow: Part 1. Determination of local concentration by statistical analysis of particle passages through crossed light beams," *J. Fluid Mech.*, vol. 14, pp. 115-135 (1962).

Segre, G., et al., "Behavior of macroscopic rigid spheres in Poiseuille flow: Part 2. Experimental results and interpretation," *J. Fluid Mech.*, vol. 14, pp. 136-157 (1962).

Seo, Jeonggi, et al., "Disposable integrated microfluidics with SELF-aligned planar microlenses," *Sensors and Acutators B*, vol. 99, pp. 615-622 (2004).

Stanley, S.L., "Amoebiasis, " *Lancet*, 361:1025-1034 (2003).

Stone, H.A., et al., "Engineering Flows in Small Devices: Microfluidics Toward a Lab-on-a-Chip," *Annu. Rev. Fluid Mech.*, 36:381-411 (2004).

Tearney, G. J., et al., "Scanning single-mode fiber optic catheter-endoscope for optical coherence tomography," *Optics Letters*, 21:543-545 (1996).

Zheng et al., "Improving Weak-Signal Identification via Predetection Background Suppression by a Pixel-Level, Surface-Wave Enabled Dark-Field Aperture," *Optics Letters*, 35(15):2636-2638 (2010).

Zheng et al., "Surface-Wave-Enabled Darkfield Aperture: A method for suppressing background during weak signal detection," *PNAS* 107 (60):9043-8, (2010).

International Search Report in International Application No. PCT/US2005/016876 mailed on Oct. 16, 2006.

Written Opinion in International Application No. PCT/US2005/016876 mailed on Oct. 16, 2006.

International Search Report in International Application No. No. PCT/US2008/054908 mailed on Aug. 26, 2008.

Written Opinion in International Application No. PCT/US2008/054908 mailed on Aug. 26, 2008.

International Search Report in International Application No. PCT/US2009/036045 mailed on Apr. 23, 2009.

Written Opinion in International Application No. PCT/US2009/036045 mailed on Apr. 23, 2009.

International Search Report in International Application No. PCT/2009/036052 mailed on Jun. 29, 2009.

Written Opinion in International Application No. PCT/2009/036052 mailed on Jun. 29, 2009.

European Patent Office (EPO) European Supplementary Search Report in EP Application No. 05 74 9488.2 mailed on Jan. 26, 2012.

European Patent Office (EPO) Office Action in EP Patent Application No. 05 749 488.2 mailed on Jun. 27, 2012.

European Patent Office (EPO) European Supplementary Search Report in EP Patent Application No. 08730664.3 mailed Feb. 7, 2012.

Japanese Patent Office (JPO) Office Action in JPO patent Application No. 2007-515164 dated Jul. 26, 2011.

Japanese Patent Office (JPO) Office Action in JPO patent Application No. 2007-515164 May 8, 2012.

Japanese Patent Office (JPO) Office Action in JPO patent Application No. 2009-553675 Jan. 24, 2012.

United States Patent and Trademark Office (USPTO) Office Action in U.S. Appl. No. 11/125,718 mailed on Nov. 14, 2008.

United States Patent and Trademark Office (USPTO) Final Office Action in U.S. Appl. No. 11/125,718 mailed on Jul. 1, 2009.

United States Patent and Trademark Office (USPTO) Notice of Allowance in U.S. Appl. No. 11/125,718 mailed on Mar. 11, 2010.

United States Patent and Trademark Office (USPTO) Office Action in U.S. Appl. No. 12/797,132 mailed on Oct. 15, 2010.

United States Patent and Trademark Office (USPTO) Office Action in U.S. Appl. No. 11/686,095 mailed on Jan. 10, 2008.

United States Patent and Trademark Office (Uspto) Office Action in Patent Application U.S. Appl. No. 11/686,095 mailed on Jul. 17, 2008.

United States Patent and Trademark Office (USPTO) Office Action in U.S. Appl. No. 11/686,095 mailed on Feb. 26, 2009.

United States Patent and Trademark Office (USPTO) Final Office Action in U.S. Appl. No. 11/686,095 mailed on Oct. 28, 2009.

United States Patent and Trademark Office (USPTO) Notice of Allowance in U.S. Appl. No. 11/686,095 mailed on Feb. 25, 2010.

United States Patent and Trademark Office (USPTO) Office Action in U.S. Appl. No. 12/785,635 mailed on Oct. 15, 2010.

United States Patent and Trademark Office (USPTO) Restriction Requirement in U.S. Appl. No. 12/398,050 mailed on Aug. 10, 2011.

United States Patent and Trademark Office (USPTO) Office Action in U.S. Appl. No. 12/398,050 mailed on Nov. 14, 2011.

United States Patent and Trademark Office (USPTO) Notice of Allowance in U.S. Appl. No. 12/398,050 mailed on Jul. 17, 2012.

United States Patent and Trademark Office (USPTO) Notice of Allowance in U.S. Appl. No. 12/398,050 mailed on Aug. 28, 2012.

United States Patent and Trademark Office (USPTO) Office Action in U.S. Appl. No. 12/638,518 mailed on Jan. 12, 2012.

United States Patent and Trademark Office (USPTO) Notice of Allowance in U.S. Appl. No. 12/638,518 mailed on Feb. 14, 2012.

United States Patent and Trademark Office (USPTO) Notice of Allowance in U.S. Appl. No. 12/638,518 mailed on Apr. 23, 2012.

United States Patent and Trademark Office (USPTO) Notice of Allowance in U.S. Appl. No. 12/638,518 mailed on Aug. 24, 2012.

United States Patent and Trademark Office (USPTO) Office Action in U.S. Appl. No. 12/398,098 mailed on May 25, 2011.

United States Patent and Trademark Office (USPTO) Office Action in U.S. Appl. No. 11/743,581 mailed on May 22, 2009.

United States Patent and Trademark Office (USPTO) Final Office Action in U.S. Appl. No. 11/743,581 mailed on Dec. 3, 2009.

United States Patent and Trademark Office (USPTO) Notice of Allowance in U.S. Appl. No. 11/743,581 mailed on Mar. 26, 2010.

United States Patent and Trademark Office (USPTO) Notice of Allowance in U.S. Appl. No. 12/823,201 mailed on Mar. 1, 2011.

United States Patent and Trademark Office (USPTO) Notice of Allowance in U.S. Appl. No. 12/823,201 mailed on Mar. 11, 2011.

United States Patent and Trademark Office (USPTO) Notice of Allowance in U.S. Appl. No. 12/792,059 mailed on Dec. 14, 2011.

* cited by examiner

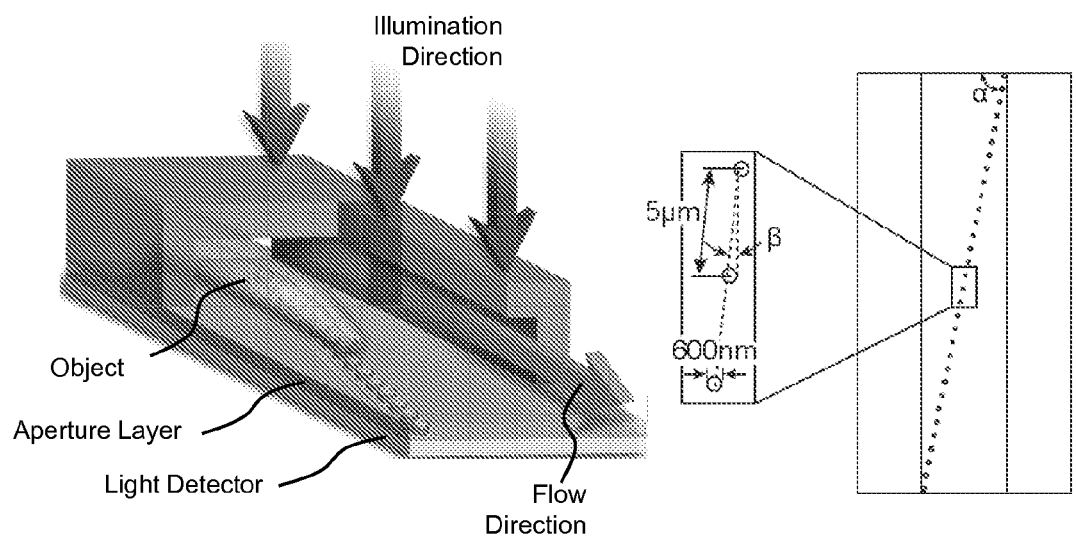
FIG. 1A                    FIG. 1B
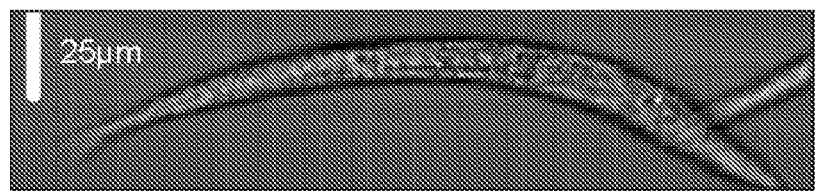
FIG. 2A
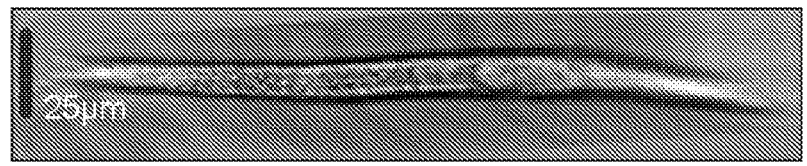
FIG. 2B
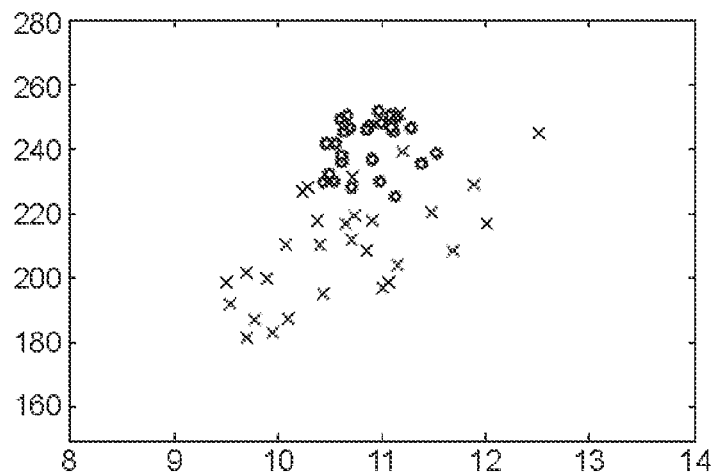
FIG. 2C

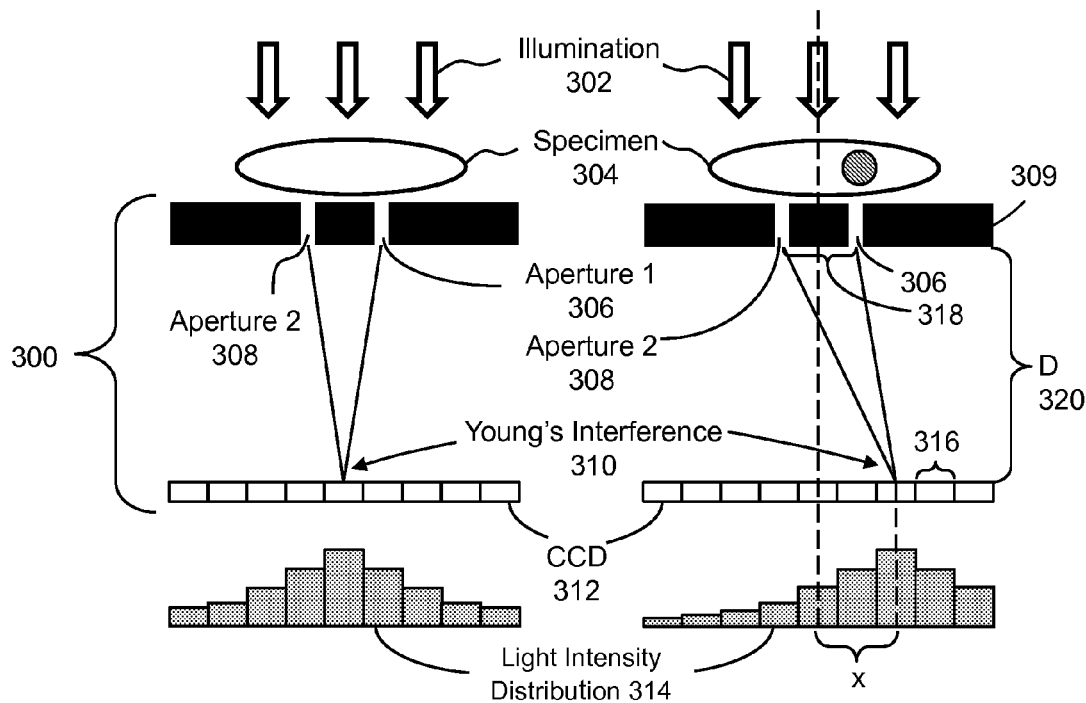

US 8,411,282 B2

ON-CHIP PHASE MICROSCOPE/BEAM PROFILER BASED ON DIFFERENTIAL INTERFERENCE CONTRAST AND/OR SURFACE PLASMON ASSISTED INTERFERENCE

CROSS-REFERENCES TO RELATED APPLICATIONS

This is a continuation application of co-pending U.S. patent application Ser. No. 12/823,201, filed on Jun. 25, 2010, which is a divisional application of U.S. patent application Ser. No. 11/743,581, filed on May 2, 2007, which is a non-provisional of and claims priority to U.S. Provisional Applications 60/796,997 and 60/796,996, filed on May 2, 2006. These applications are hereby incorporated by reference in their entirety for all purposes.

This non-provisional application is related to the following commonly-assigned patent application, which is hereby incorporated by reference in its entirety for all purposes:

U.S. patent application Ser. No. 11/686,095 entitled "Optofluidic Microscope Device" filed on Mar. 14, 2007.

STATEMENT REGARDING FEDERALLY SPONSORED RESEARCH AND DEVELOPMENT

The U.S. Government has certain rights in this invention pursuant to Grant No. HR0011-04-1-0032 awarded by DARPA.

BACKGROUND OF THE INVENTION

1. Field of the Invention

The present invention relates generally to microscopes, and in particular, to a method, apparatus, and article of manufacture for a differential interference contrast (DIC) microscope and/or light field profiler based on Young's interference. In addition, the present invention provides a method, apparatus, and article of manufacture for an optofluidic microscope that is surface plasmon assisted. Both methods are related in that they make novel usage of interference between holes and/or structured holes to enable higher sensitivity and a different contrast method in on-chip microscopy imaging and light field profiling.

2. Description of the Related Art (Note: This application references a number of different publications as indicated throughout the specification by reference numbers enclosed in brackets, e.g., [x]. A list of these different publications ordered according to these reference numbers can be found below in the section entitled "References." Each of these publications is hereby incorporated by reference in its entirety for all purposes.)

Differential Interference Contrast (DIC) Microscopes

A major problem of imaging transparent specimens with conventional microscopes is that it can be difficult to elicit contrast, because the imaging technique is solely based on the amplitude information provided by the sample. This difficulty is especially true for most of the biological samples. Therefore phase information, if measured, will improve the imaging contrast dramatically. Differential interference contrast (DIC) microscope performs admirably in this respect by rendering excellent phase contrast in transparent specimens, and is widely used in biology and clinical laboratories.

DIC microscopes are a beam-shearing interference system [DIC1]. A reference beam is sheared by a very small distance with respect to a sample beam. The phase difference between the reference beam and the sample beam after they pass two adjacent spots of the specimen provides the differential phase contrast of the specimen. Since DIC microscopy is an interference-based technique, it can distinguish minuscule amount of phase differences and identify small changes in the sample's refractive index.

Prior art DIC microscopes have some disadvantages. Firstly, prior art DIC microscopes are very expensive instruments, as many complicated and expensive optical components are required to manipulate the light. Secondly, the lateral resolution of current DIC microscopes is determined by the spot size of the objective lens of the DIC microscope, which has a diffraction limit. The small sheared distance between the reference beam and the sample beam is usually tuned to be slightly smaller than this spot size.

Microfluidics

Recent developments in microfluidics have brought forth a variety of new devices that can potentially revolutionize traditional biomedical and chemical experiments [MICRO2-MICRO7]. One such new device is the optofluidic microscope (OFM) described in U.S. patent application Ser. No. 11/686,095, filed on Mar. 14, 2007, by Changhuei Yang and Demetri Psaltis, entitled "OPTOFLUIDIC MICROSCOPE DEVICE," which is incorporated by reference herein. The OFM fuses the advantage of optical imaging in providing high resolution and the advantages of microfluidics, such as low cost and high throughput. Further, OFM's application in nematode imaging and phenotyping has been reported [MICRO8].

FIGS. 1A and 1B illustrate an OFM device that consists of an opaque metallic film with an etched array of submicron holes. The metallic film is bonded to the floor of a PDMS (polydimethylsiloxane) microfluidic chip. The hole array is oriented at a small angle relative to the micro-channel (FIG. 1B). As a biological sample passes over the nanohole array (as indicated by the flow direction), each individual hole will take a line scan of the target. The sample is illuminated based on the illuminated direction indicated. FIG. 1B illustrates the top view of the OFM wherein α denotes the isolated hole and β denotes the corresponding hole that scans the same line on the target as hole α does.

The OFM was used to image and perform nematode phenotype characterization of Wild type *C. elegans* and dpy-24 mutants at their first larval stages as illustrated in FIG. 2. FIG. 2(*a*) illustrates the OFM image of the wild-type *C elegans* larvae at the first larval stage. FIG. 2(*b*) illustrates the OFM image of a dpy-24 mutant. FIG. 2(*c*) illustrates the aspect ratio of wild-type larvae and dpy-24 mutants.

The resolution limit of OFM and any other nanohole based sensors is given by the hole size. Although smaller hole size gives better optical resolution, the optical transmission through the nanohole will be dramatically reduced [MICRO9 and MICRO10]. The weak transmission signal may be buried by electronic noise or background noise, which can make an isolated subwavelength hole less desirable for optical imaging applications. Although powerful lasers can help to increase the total transmission through the nanohole, high-intensity light may also have adverse effects on the biological samples. Therefore, new schemes that can either enhance the optical transmission of a nanohole or improve the sensitivity of the detection are desirable.

In view of the above, what is needed is the ability to overcome the disadvantages of the prior art DIC microscopes and to improve the capability and sensitivity of optofluidic microscopes.

SUMMARY OF THE INVENTION

One or more embodiments of the invention provide a novel DIC microscope and/or light field profiler based on Young's interference. It is a simple Young's interference setup and no complicated and expensive optical components are involved. As such, the invention is less expensive and more robust than the conventional DIC microscope. In one or more embodiments of the DIC microscope and/or light field profiler, the reference beam and the sample beam are selected by two adjacent apertures. The lateral resolution is not limited by diffraction limit of the objective lens, but is instead determined by the distance between the two adjacent apertures. This distance can be subwavelength.

In addition, commercially available DIC microscopes have limitations in imaging the samples that have anisotropic refractive index distribution such as bones and teeth. As the tiny beam spots on the adjacent parts of the sample have orthogonal polarizations, any change in the linear polarization caused by the optical anisotropy of the sample will possibly render a wrong phase relationship when these two polarized beams are combined together to generate an interference signal. However embodiments of the invention will not suffer from such improper phase relationships because the reference and sample beams have the same polarization. Another feature of one or more embodiments is that the simplicity of the invention enables easy integration of the invention on a chip, thereby providing an implementation as an on-chip DIC microscope.

In addition to the above, embodiments of the invention improve the detection sensitivity of the optofluidic microscope by using a periodically corrugated surface. Further, the excitation of surface waves, or surface plasmons (SP), on metallic surfaces enhances the transmission through nanoholes in a microfluidic microscope.

BRIEF DESCRIPTION OF THE DRAWINGS

Referring now to the drawings in which like reference numbers represent corresponding parts throughout:

FIGS. 1A and 1B illustrate an optofluidic microscope device that consists of an opaque metallic film with an etched array of submicron holes;

FIG. 2(a) illustrates an OFM image of the wild-type *C elegans* larvae at the first larval stage;

FIG. 2(b) illustrates an OFM image of a dpy-24 mutant;

FIG. 2(c) illustrates the aspect ratio of wild-type larvae and dpy-24 mutants;

FIGS. 3A and 3B shows the configuration of a DIC microscope based on Young's interference and the operating principle in accordance with one or more embodiments of the invention;

DETAILED DESCRIPTION OF THE PREFERRED EMBODIMENTS

Figure 4:
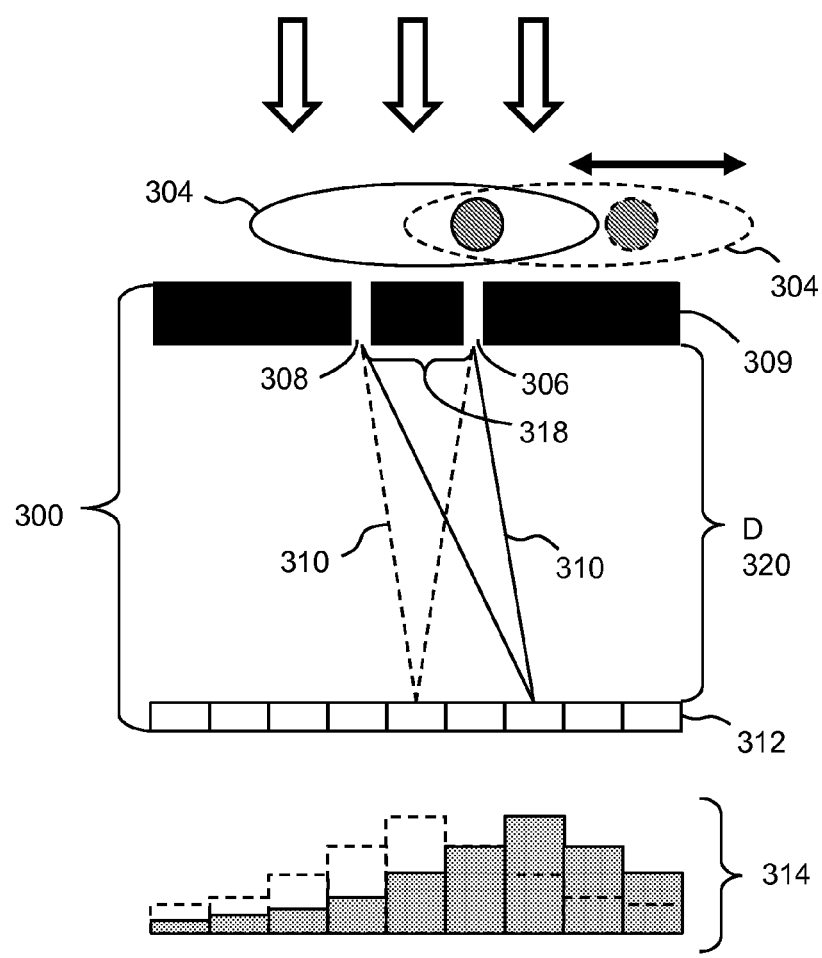
FIG. 4 illustrates a scanning of a specimen on a DIC microscope in accordance with one or more embodiments of the invention.

In the following description, reference is made to the accompanying drawings which form a part hereof, and which is shown, by way of illustration, several embodiments of the present invention. It is understood that other embodiments may be utilized and structural changes may be made without departing from the scope of the present invention.

Overview

Embodiments of the invention provide a differential (DIC) microscope and beam profiler based on Young's interference. In addition, embodiments of the invention provide a surface plasmon assisted method that utilizes corrugation to enhance a high resolution transmission signal and can provide a different type of image contrast. For example, this method can be used to generate dark field images.

Differential Interference Contrast (DIC) Microscope/Light Field Profiler Based on Young's Interference FIGS. 3A and 3B shows the configuration of a DIC microscope based on Young's interference and the operating principle in accordance with one or more embodiments of the invention.

The DIC microscope 300 consists of two main parts for a Young's interference setup based on two apertures 306 and 308 (i.e., of metal film 309) and a photo detector 312 (e.g., CCD [charge-coupled device], CMOS [complimentary metal-oxide semiconductor], PSD [photo-sensitive photodetector], etc.).

Aperture 1 306 may be used to sample the reference beam from the specimen 304, and aperture 2 308 may be used to sample the sample beam from the specimen 304. If the reference beam and the sample beam pass a homogenous region of the specimen 304, the reference beam and the sample beam carry the same phase. When the reference and sample beams exit from the two apertures 306 and 308, the light intensity distribution 314 of their Young's interference 310 is centered on the CCD 312 (as illustrated in FIG. 3A). However, if the reference beam and the sample beam pass different features in the specimen 304 (i.e., as illustrated by the reference beam passing over the nucleus in FIG. 3B), the beams will carry different phases. Accordingly, when the beams exit from the two apertures 306 and 308, the light intensity distribution of their Young's interference 310 is shifted on the CCD 312. The offset is directly related to the phase difference between the reference beam and the sample beam.

As described herein, Young's interference is used to determine the phase in accordance with $$\Delta\phi \approx \frac{2\pi}{\lambda} \frac{a}{D} x,$$

wherein D is distance 320, a is distance 318, and x is the displacement with respect to the center of the apertures 304-306.

From the data of the CCD 312, the information of the differential phase contrast of the specimen 304 can be easily retrieved. In addition, the amplitude of the sample's 304 transmission at that location can be computed by simply summing up all of the signals from the CCD array 312.

To get all of the information of differential phase contrast from the whole specimen 304, one may either scan the DIC microscope 300 across the specimen 304 or scan the specimen 304 across the DIC microscope 300. FIG. 4 illustrates such a scanning of the specimen 304 in accordance with one or more embodiments of the invention.

Figure 5:
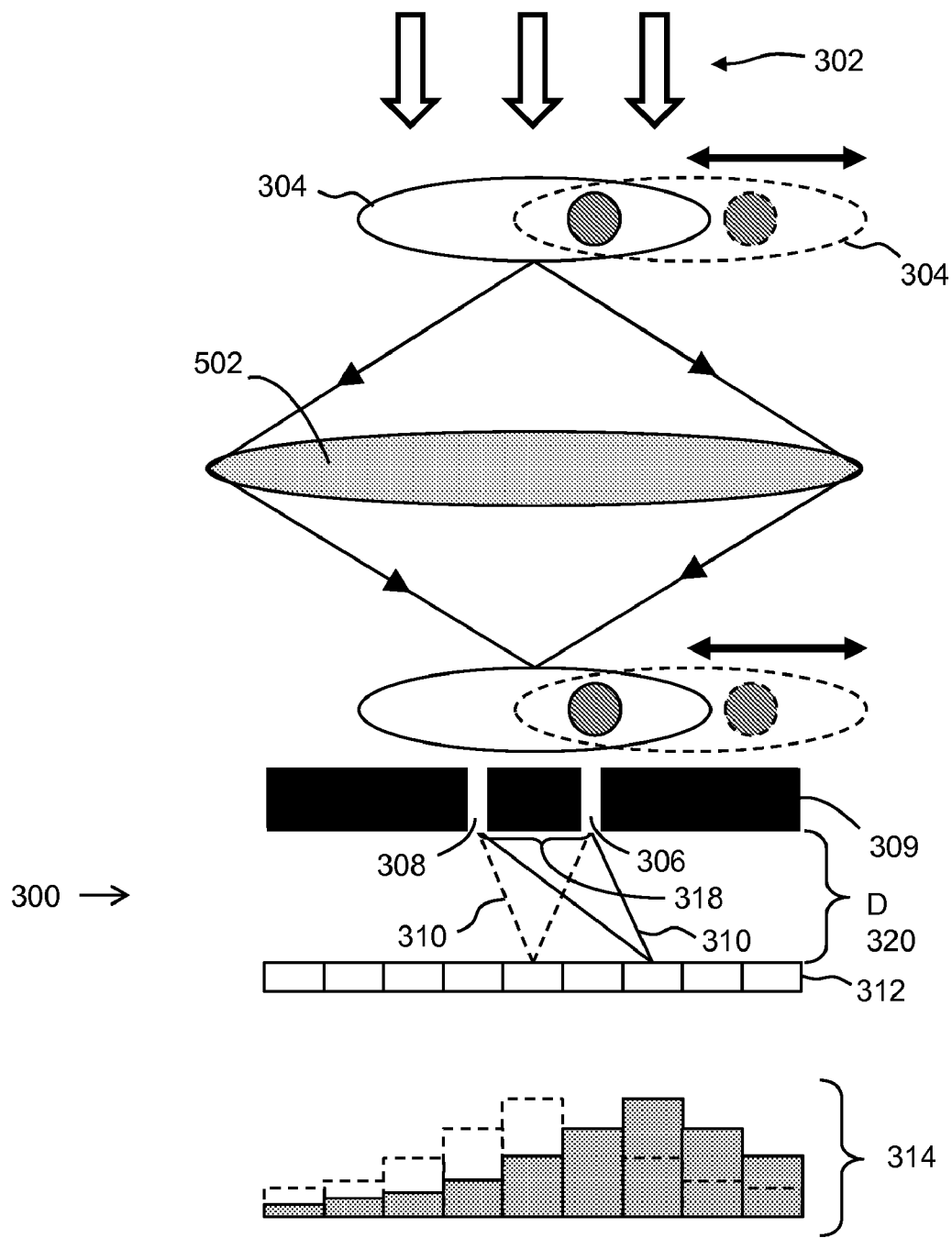
FIG. 5 illustrates a configuration of a DIC microscope in accordance with one or more embodiments of the invention.

FIG. 5 illustrates another configuration of a DIC microscope 300 in accordance with one or more embodiments of the invention. As illustrated, an optical system (i.e., lens 502) is used to project the specimen 304 onto the plane of the two interference apertures 306 and 308. The phase difference information of the specimen 304 can be decoded by the Young's interference 310 pattern on the CCD sensor 312. The image of the specimen 304 can either be scanned across the interference apertures 306 and 308 or scan the interference apertures 306 and 308 across the image of the specimen 304 to get all of the information of differential phase contrast from the whole specimen 304.

Figure 6:
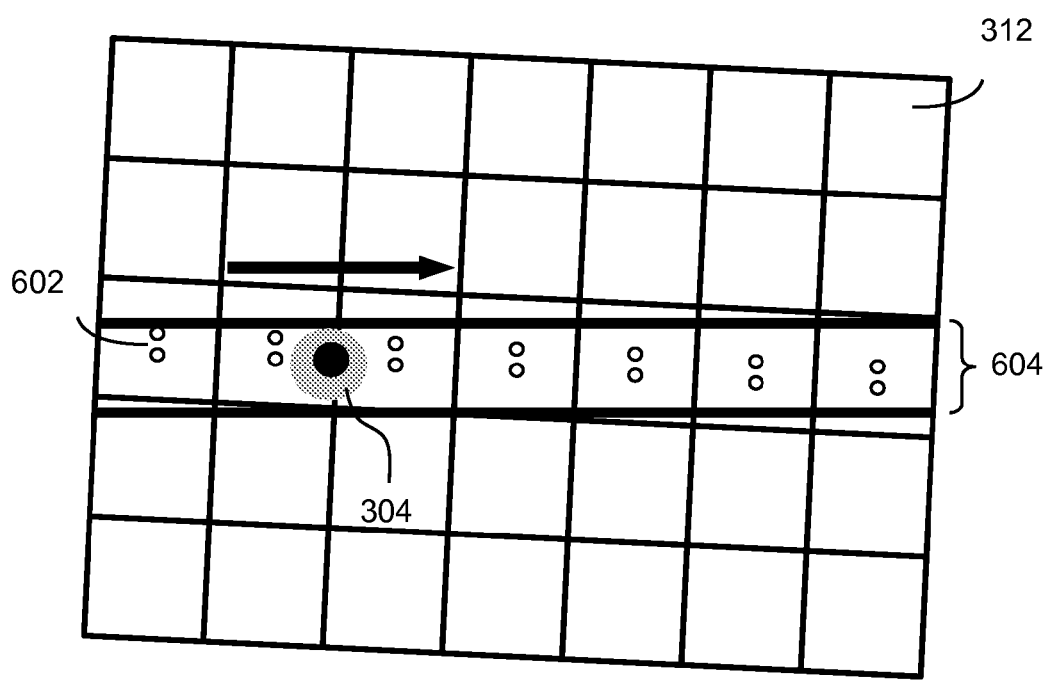
FIG. 6 illustrates an on-chip DIC imaging system of the optofluidic microscope (OFM) technique in accordance with one or more embodiments of the invention.

In addition to the above, the optofluidic microscope (OFM) technique[DIC2] (and that is described in copending application Ser. No. 11/686,095) can be combined with the DIC microscope 300 to implement an on-chip DIC imaging as illustrated in FIG. 6. In such a scheme, several of the DIC hole pairs 602 can be fabricated in series on a 2D CCD sensor array 312. There may be a gap between the array of holes 602 and the sensor (see FIG. 1A) so that the transmission can freely propagate and enable the light field (i.e., illumination) directionality to be manifested as a lateral shift. The specimen may then flow across the DIC microscope 300 through the microfluidic channel 604. Each DIC microscope 300 can obtain a DIC line scan of the specimen 304. Using the reconstruction algorithm of the OFM, the whole DIC information about the specimen 304 can be obtained by simply letting the specimen 304 flow across the DIC microscope array (e.g., through the microfluidic channel 604).

As illustrated in FIG. 6, the CCD sensor array 312 represents pixels. In one or more embodiments, for each 10×10 pixel group, a single pixel is provided with a hole pair 602 in the center of each pixel. Thus, there are two holes per pixel. Further, the microfluidic channel 604 is oriented at an angle with respect to the pixels. Accordingly, the two holes 602 are centered over the pixel while the microfluidic channel 604 is angled over the pixels. Such an arrangement, provides the ability to better determine DIC information about the specimen 304 (e.g., via analysis of the light intensity distribution 314) while the specimen 304 flows across the channel 604.

Figure 7:
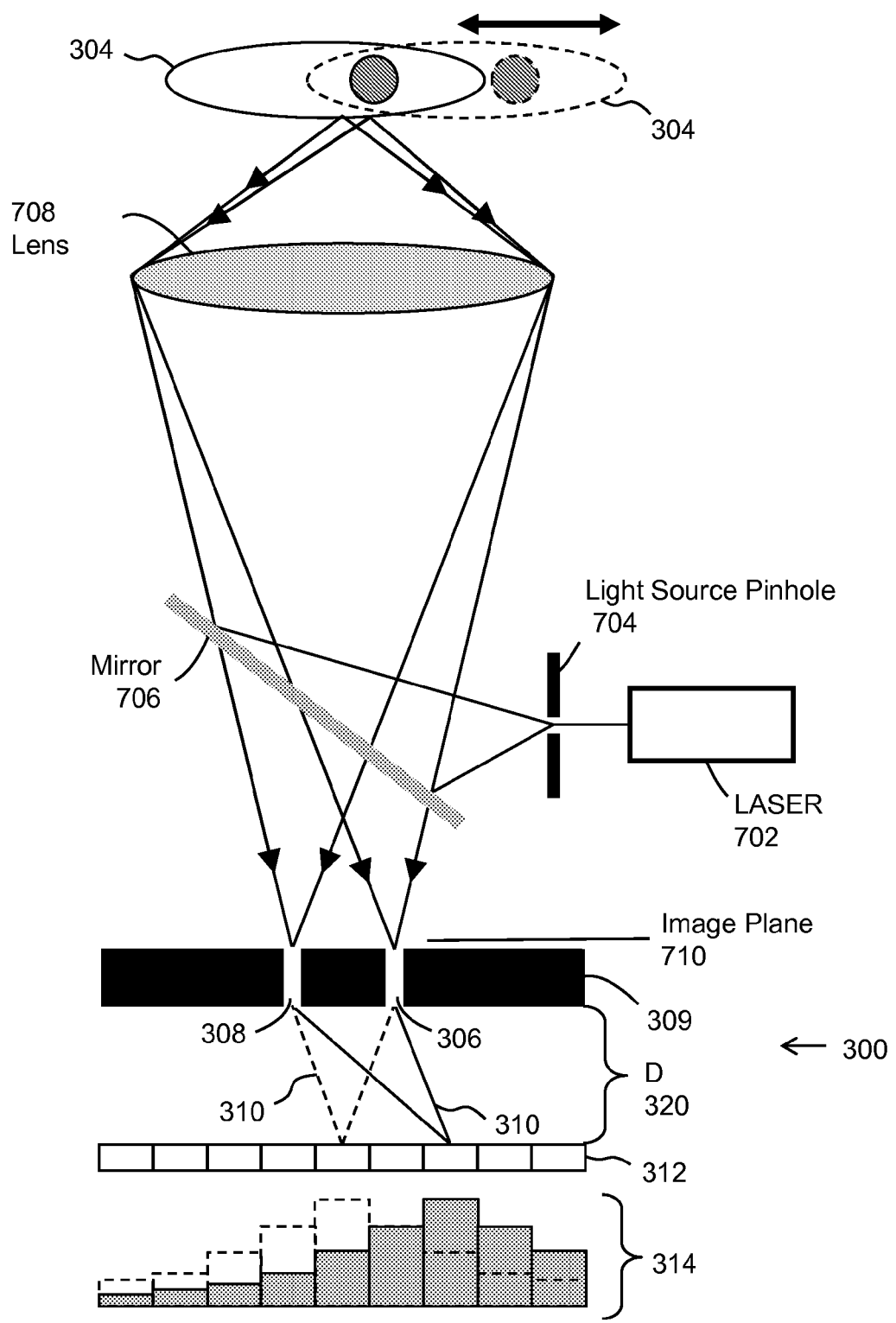
FIG. 7 illustrates a confocal microscope technique combined with a DIC microscope to implement a confocal DIC imaging microscope in accordance with one or more embodiments of the invention.

Embodiments of the invention may also combine the confocal microscope technique [DIC3] with the DIC microscope (described above) to implement a confocal DIC imaging microscope as illustrated in FIG. 7. If the DIC microscope (i.e., item 300 of FIG. 3) is applied to the setup similar to a confocal microscope, the interference apertures 306-308 in the DIC microscope 300 can act as a spatial filter as the detector pinhole in confocal microscope.

The difference between the prior microscopes described herein and the confocal DIC imaging microscope of FIG. 7 is that there are two spatial filter pinholes (i.e., as the apertures 304-306), which can grab information from two 3D localized spots in the specimen 304 simultaneously. The phase difference information between these two spots also can be decoded by the Young's interference pattern 310 on the CCD sensor 312. Accordingly, the 3D information of the differential phase contrast may be obtained from the specimen.

As illustrated in FIG. 7, the laser 702 passes through the light source pinhole 704 and is reflected by the mirror 706 and the lens 708 to illuminate the specimen 304. Accordingly, FIG. 7 illustrates a reflective mode microscope since the light that is used to illuminate the object plane 304 from the bottom while maintaining the image plane 710 immediately above the apertures 304-306.

In the above descriptions, the CCD device 312 may be described as the sensor. However, CMOS, position sensitive device (PSD) or other kinds of photo detectors can be used as sensors.

Referring again to FIGS. 3A and 3B, it may be noted that the sensitivity of the differential phase detection in the DIC microscope (described herein) may be determined by the distance 318 between two interference apertures 304-306, the distance 320 between the interference apertures 304-306 and the photo detector 312, and the position sensitivity 316 of the photo detector. A spacer or a means/mechanism that provides the desired spacing 320 may be used. Further, the lateral resolution of the DIC microscope 300 may be determined by the distance 318 between the two apertures 304-306. Proper care in the design should be taken to meet to the requirement of the specific application.

In view of the above, the position sensitivity and (i.e., the size of each pixel 316) may be 10 microns in size while each hole/aperture 304 and 306 may be 500 nanometers. In addition, the distance 318 between apertures 304-306 may also be 500 nanometers. Further, the distance 320 between the aperture plane and the CCD 312 may be 100 microns. In an alternative embodiment such as an on-chip DIC phase imager based on Young's interference, the aperture imaging film may be 0.2 μm and distance 320 may be 120 μm while the separation distance 318 may be 1 μm. In yet another on-chip DIC phase image based on Young's interference, the distance 320 may be 0.5 μm, with a separation 318 of 1 μm. Such spacing and measurements provide the ability to determine the sensitivity/accuracy of the differential phase detection.

Potential applications of embodiments of the invention include inexpensive high resolution and more capable DIC imaging as well as on-chip DIC imaging devices. In addition, the measurement of phase may be used in various contexts such as an interferometer/DIC microscope or as a Wavefront sensor/Shack Hartmann device.

Using embodiments of the invention, a Gaussian laser beam or an optical vortex may also be profiled. The quantitative measurement of laser beam profiles may be useful for ensuring the efficient and accurate use of lasers in applications ranging from laser machining to fiber optics to LASIK surgery. In addition, precise knowledge of the focal field distribution of high-NA lenses may be important in the design of systems such as confocal laser scanning microscopy and optical serial sectioning microscopy.

Figure 8:
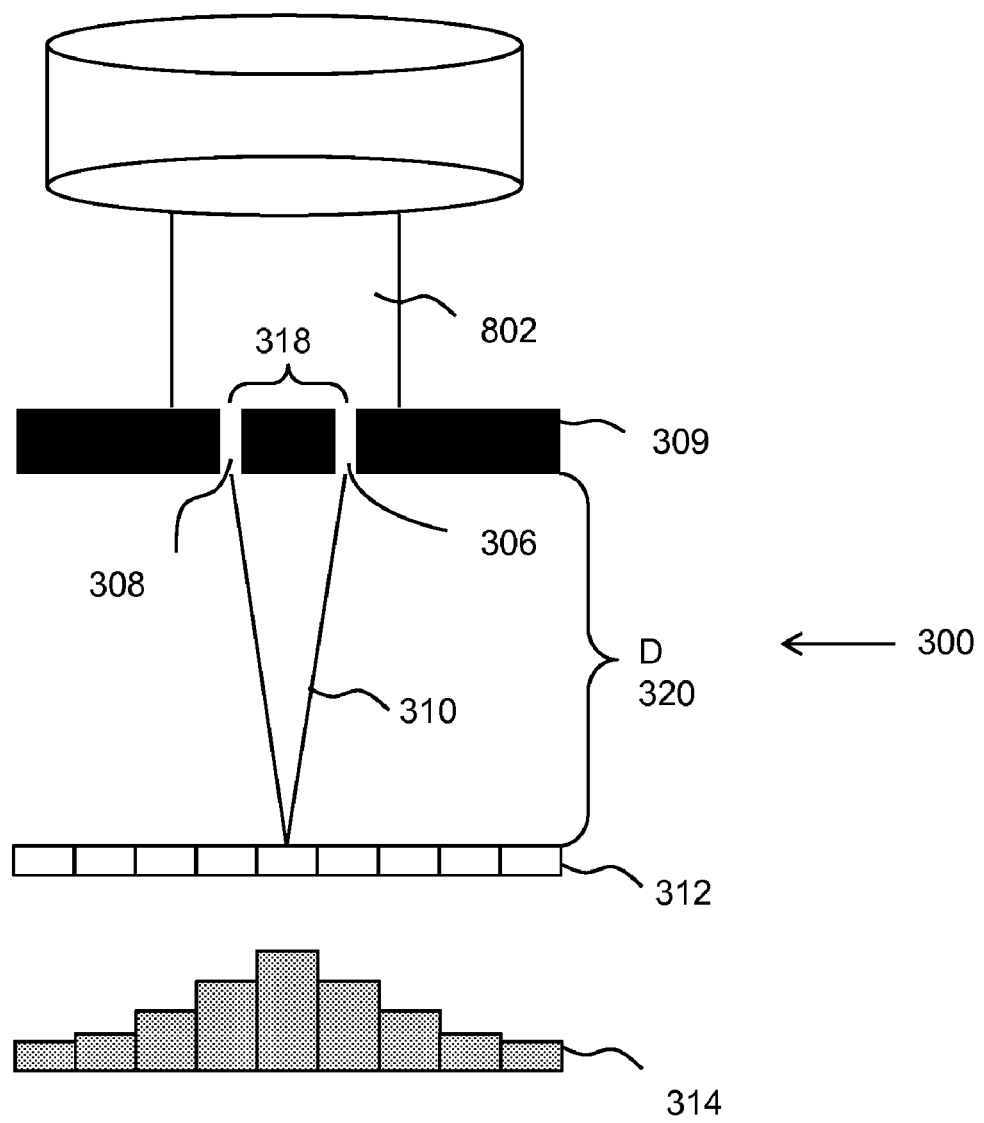
FIG. 8 illustrates a single axis on-chip DIC phase beam profiler in accordance with or more embodiments of the invention.
Figure 9:
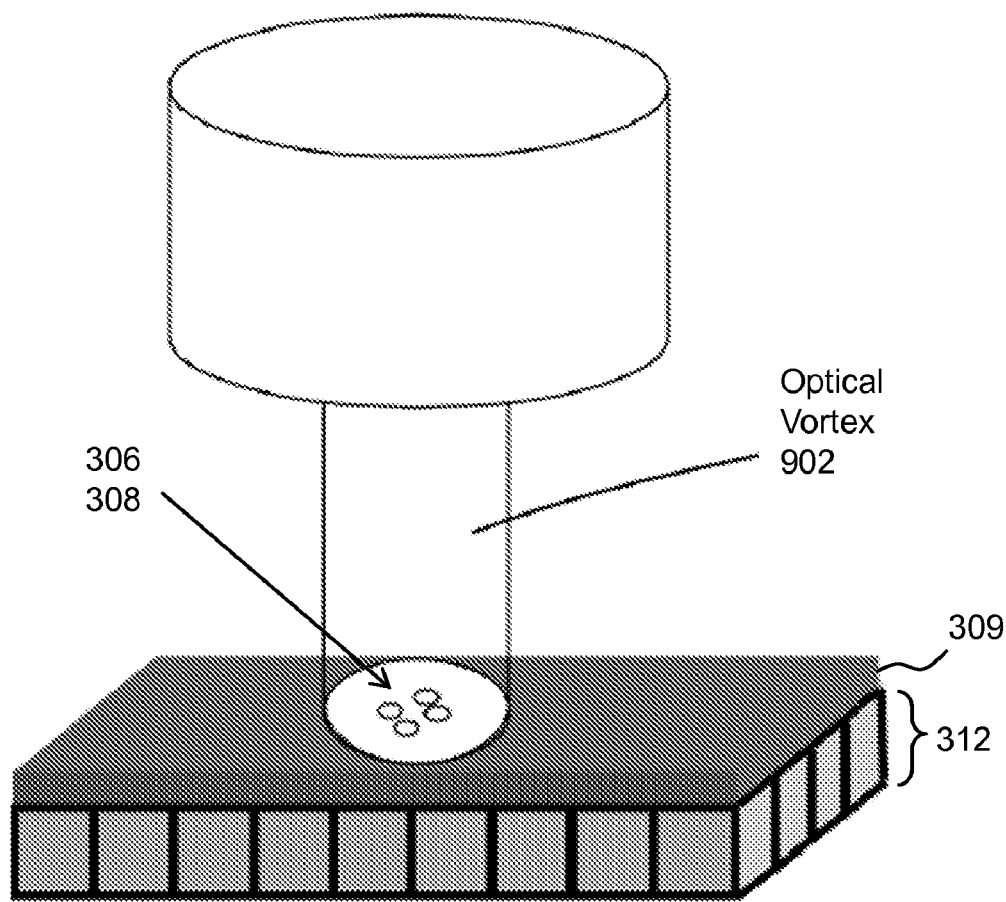
FIG. 9 illustrates a dual axes DIC that may be used in accordance with one or more embodiments of the invention.

FIG. 8 illustrates a single axis on-chip DIC phase beam profiler in accordance with or more embodiments of the invention. Rather than illuminating a specimen as illustrated in FIG. 3-6, a single axis laser beam 802 may be projected onto the apertures 306-308. Four apertures 306-308 may also be used to create a dual axes on-chip DIC phase beam profiler in accordance with one or more embodiments of the invention. FIG. 9 illustrates a dual axes DIC that may be used in accordance with one or more embodiments of the invention. As illustrated the optical vortex 902 from the beam is shown through four apertures onto a photodetector device (e.g., CCD 312).

In addition to the above, a high-resolution portable beam profiler may be based on a slanted linear array of small apertures, termed a slanted hole array beam profiler (SHArP). Apertures may be directly fabricated on a metal-coated CMOS imaging sensor. With a single linear scan, the aperture array can establish a virtual grid of sampling points for beam profiling. The size of the apertures can be adjusted to increase/improve resolution. Such a methodology is further described in [DIC5].

In addition, to the above, it may be noted that a DIC microscope may be qualitative and non-linear in nature. In this regard, a DIC image may be a mix of amplitude and phase information. Accordingly, it may be useful to obtain the actual phase, instead of a directional phase gradient. Embodiments of the invention provide a non-iterative and robust phase reconstruction method. Such a method may apply a Fourier-space integration approach that is direct, straightforward and reasonably accurate for images that do not contain discontinuities (e.g., biological phase images) [DIC4].

Figure 10:
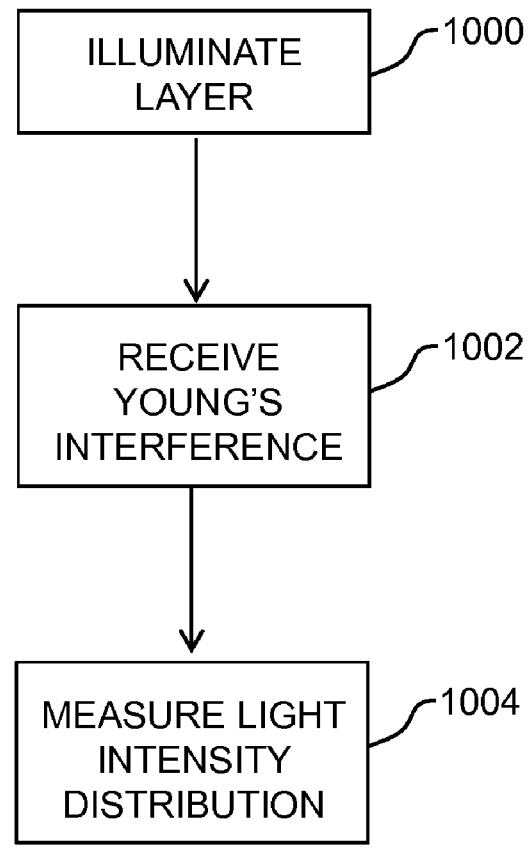
FIG. 10 is a flow chart illustrating a method for determining phase in accordance with one or more embodiments of the invention.

FIG. 10 is a flow chart illustrating a method for determining phase in accordance with one or more embodiments of the invention. At step 1000, a layer is illuminated wherein the layer has at least one pair of two apertures. In a DIC microscope embodiment, a sample may placed between the illuminating source and the layer. Further, the sample may be moved across the apertures in the layer (or the microscope can be moved across the sample). Alternatively, a lens may be used to project the specimen onto a plane of the pair of apertures. In an alternate embodiment (e.g., in a beam profiling device), the layer may be illuminated by a laser beam.

At step 1002, Young's interference from the illumination passing through the pair of two apertures is received on a photodetector.

At step 1006, the might intensity distribution is measured on the photodetector. As described above, a specimen may be placed between the illuminating source and the layer and a differential phase contrast of the specimen is determined by the light intensity distribution (i.e., received/measured by the photodetector). In a phase beam profiling embodiment, a beam profile of the laser beam is determined based on the light intensity distribution measured by the photodetector. It should be noted that a similar embodiments and method may be utilized to produce a light field profiler in accordance with one or more embodiments of the invention.

Alternatively, in an optofluidic DIC microscope embodiment, the specimen may be passed through a body that has a fluid channel with the layer as a surface. In such an embodiment, multiple pairs of two apertures are fabricated in series on the layer. Further, the photodetector is a two-dimensional (2D) sensor array with a single corresponding element of the 2D array configured to receive the Young's interference from each pair of two apertures. To create the Young's interference, a gap exists between the layer and the photodetector. The specimen flows in the fluid channel across the multiple pairs of two apertures and each corresponding element of the 2D sensor array receives a line scan of the specimen.

In addition to the above, in either phase-beam profiling embodiment or a DIC microscope embodiment, the device may be fabricated/implemented in an on-chip device.

Surface Plasmon Assisted Optofluidic Microscope/Light Field Profiler

As described above, an optofluidic microscope and/or light field profiler may be used to provide high resolution with low cost and high throughput. However, the optical transmission through the nanoholes is problematic in that as the resolution increases (i.e., by using smaller nanoholes/apertures), a weaker transmission signal is received that cannot be easily isolated for use in optical imaging applications. Embodiments of the present invention enable increased resolution while maintaining the ability to accurate isolate and measure a transmission signal. Such increased resolution and enhanced transmission capabilities are provided by corrugating the surface of the metal in which the apertures are located. In this regard, grooves are etched in the metal to corrugate the surface. Different embodiments of the invention may corrugate the surface in different patterns.

Dark Field OFM and Improvement of the Detection Sensitivity

Optical transmission through a nanohole on a periodically corrugated surface has been examined in the prior art. Both transmission enhancement and suppression have been observed [MICRO11, MICRO12]. Henri Lezec and his colleagues ([MICRO1]) used a new model called composite diffracted evanescent waves (CDEWs) to explain the unexpected transmission suppression. Such phenomenon may also be explained by surface plasmons. The suppression of the optical transmission through a nanohole occurs when there is destructive interference between the optical wave coming through the nanohole and the optical wave that is channeled in from the peripheral surface plasmon waves.

Figure 11:
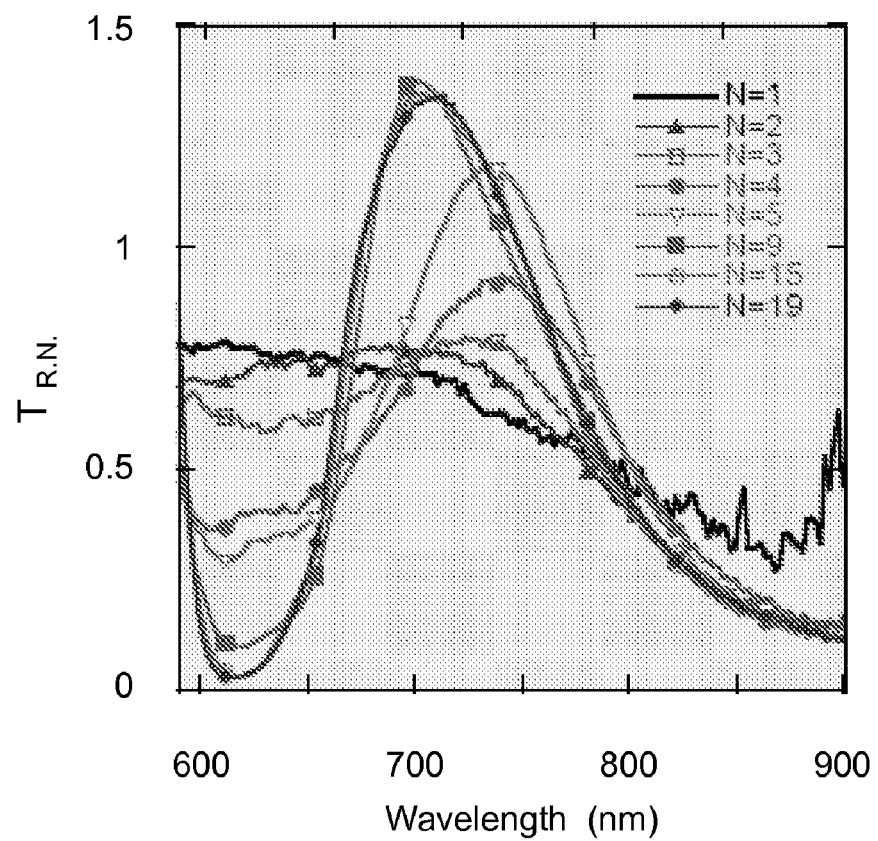
FIG. 11 illustrates an abnormal transmission of a square nanohole array for visible and near-IR light in accordance with one or more embodiments of the invention.

FIG. 11 illustrates an abnormal transmission of a square nanohole array (physically similar to one nanohole on a corrugated surface) for visible and near-IR light. The value of N corresponds to the number of nanoholes in a row and a column. The phenomenon of the transmission suppression can be used in one or more embodiments of the invention based on an optofluidic microscope (OFM) setup and can help improve the optical detection.

Figure 12:
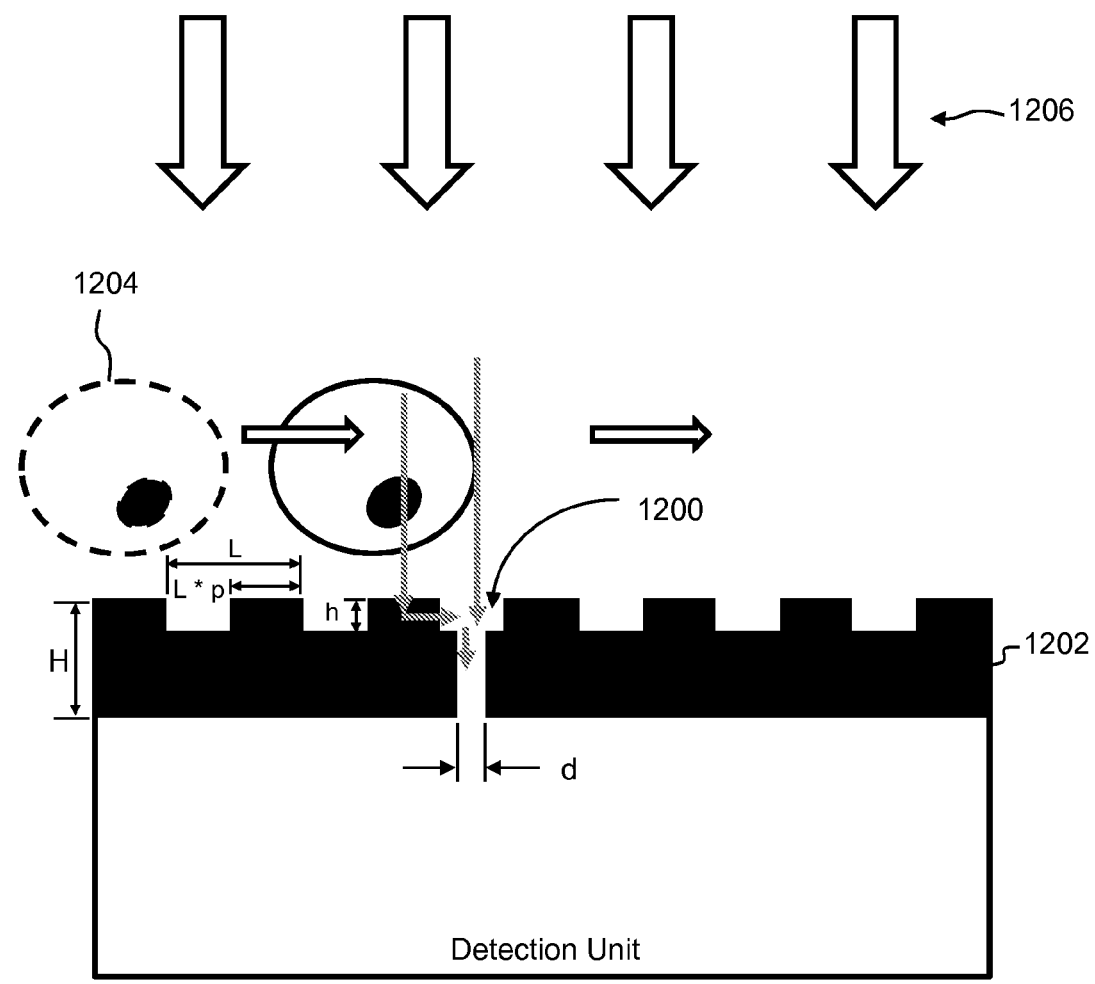
FIG. 12 illustrates a corrugated surface an nanohole on a layer configured in accordance with one or more embodiments of the invention.

FIG. 12 illustrates a nanohole 1200 with diameter d etched through a corrugated surface 1202 (period: L, duty cycle: p, depth: h, thickness: H). As illustrated, the nanohole 1200 of diameter d is used as an imaging probe while the specimen 1204 passes through the fluid channel having the corrugated surface 1202. The corrugated surface 1202 can be made in an opaque silver or aluminum film by using electron beam lithography or focused ion beam (FIB). A continuous wave (cw) laser at single wavelength at normal incidence provides the illumination 1206.

The transmission of the nanohole 1200 on the corrugated surface 1202 in the visible band and IR band was studied by Lezec et al [MICRO11]. At a specific wavelength ($\lambda_0$), optical transmission is at minima and is apparently weaker than that of an isolated nanohole (as can be seen in FIG. 11). In the context of OFM, when there is no sample 1204 present, the detector receives a minimum amount of photons and only gives a weak dark field signal.

When a sample 1204 passes over the nanohole 1200 array by use of microfluidic driven flow, it will introduce changes in the amplitude and phase of both the optical wave directly through the nanohole 1200 and the surface plasmon wave on its peripheral. The condition of destructive interference no longer holds, and the transmission is expected to increase from the minimum value which indicates the presence of a sample 1204. This detection scheme is similar to dark field optical microscopy where the illumination background is originally dark and the introduction of optical discontinuity of the sample 1204 makes it look bright on a dark background. This technique has a signal to noise sensitivity advantage over bright field geometry.

In accordance with one or more embodiments of the invention, a spherical cell 1204 may be used to explain the operations of dark-field OFM. In FIG. 12, a laser source provides a uniform illumination 1206 on the plane of the nanohole 1200 region. The parameters of the corrugated surface 1202 are selected such that the transmission of the nanohole 1200 is suppressed. As was described above, such a suppression is caused by the destructive interference between optical wave transmitted directly through the hole 1200 and the peripheral surface waves. Therefore, the signal detected by the detection unit underneath the metallic layer/corrugated surface 1202 will be weak. The detection unit can be a CMOS sensor directly attached to the metallic layer 1202 or a microscope relay system that maps the transmission of the nanohole 1200 onto a linear sensor array.

Now, consider the situation where a cell 1204 passes over the nanohole 1200 by an appropriate microflow driving scheme, such as electrokinetics, pressure gradient or dielectrophoresis. When the cell 1204 is far away from the nanohole 1200, the cell 1204 has negligible impact on changing the destructive interference condition between the optical wave and the surface wave. Thus, the detector's signal remains weak. However, when the cell 1204 arrives at the nanohole 1200, the cell 1204 will change the intrinsic phase of one or both of the two electromagnetic waves. This change is due to the slight optical property discontinuity (e.g. refractive index, absorption coefficient) between water and the cell 1204. Note that the discontinuity in optical property between cell 1204 and water is subtle and may have little effect in bright field microscope. However, in dark-field OFM, the accumulated phase shift disrupts the original condition of destructive inference, and thus the optical transmission signal will become much stronger, which will be readily registered by the detector as a signal change.

Various schemes may be used to implement one or more embodiments of the invention using dark field microscopy. The goal of such schemes is to create a corrugated surface/grating factor $G_m$ having a defined period (e.g., via an etching and/or fabrication process) such that the surface plasmon polariton $\overline{K_{spp}}$ is equal to the optical wave on the surface (parallel) $\overline{K}$:

$$\overline{K_{spp}} = \overline{K} + \overline{G_m}$$

A constant value $\overline{\beta}$ may also be added to further enhance the resolution and transmission:

$$\overline{K_{spp}} = \overline{K} + \overline{G_m} + \overline{\beta}$$

In accordance with the above equations, various schemas may be utilized to optimize the transmission and resolution received via a nanohole. Schemas 1-4 below utilize a periodic corrugation on the top surface of the metallic film in an optofluidic microscope. Schema 5 illustrates the use of a periodic corrugation on both the top and bottom surface.

It should also be noted that the principles described herein may be utilized in a light field profiler.

Scheme 1

Figure 13:
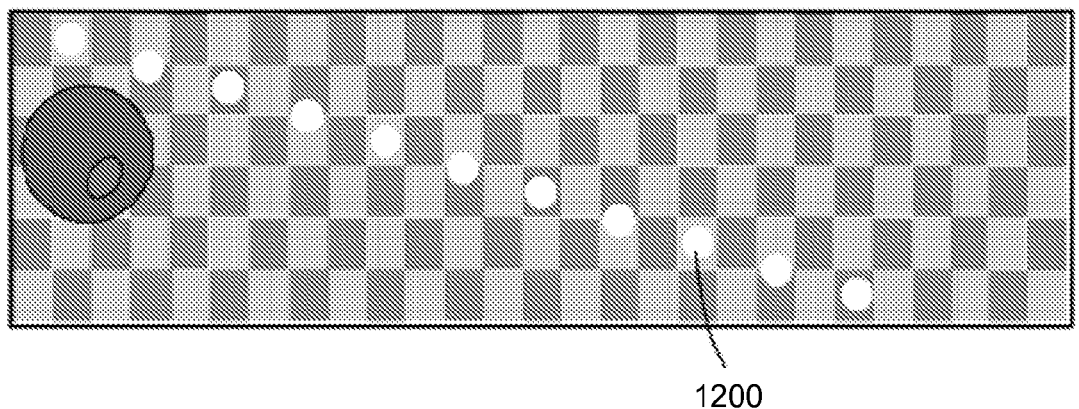
FIG. 13 illustrates a scheme wherein grey colors schematize surface corrugation that will appear different under a microscope in accordance with one or more embodiments of the invention.

FIG. 13 illustrates a scheme wherein grey colors schematize surface corrugation that will appear different under a microscope. As illustrated, the nanoholes 1200 are laid down in a slanted fashion on a background of a corrugation surface 1202 (duty cycle of dimples chosen as 50%) with a rectangular lattice. One advantage associated with such a rectangular lattice is that its fabrication on a relatively large area is simple. As the hole 1200 sizes are the same, the same "superlattice" structure will work for all of holes 1200 because the nanoholes 1200 share the same momentum conservation considerations. Such a mesh checkerboard pattern type of corrugation has been shown to enhance the transmission via the nanoholes 1200.

Scheme 2

Figure 14:
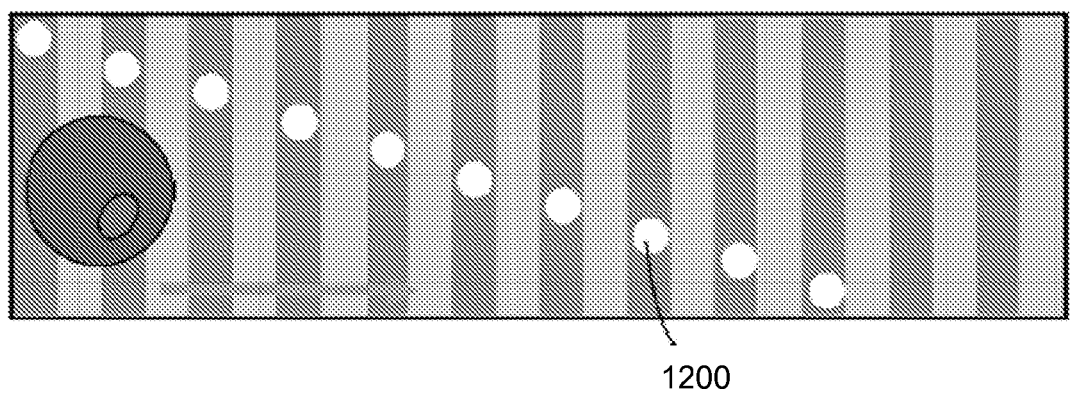
FIG. 14 illustrates a schema wherein a two dimensional rectangular lattice-structure (i.e., of FIG. 13) is replaced with a 1D grating structure in accordance with one or more embodiments of the invention.

FIG. 14 illustrates a schema wherein the two dimensional rectangular lattice-structure (i.e., of FIG. 13) is replaced with a 1D grating structure. No matter whether surface plasmon waves or surface composite diffracted evanescent waves (CDEWs) are applied to explain optical transmission suppression of the nanohole, destructive interference conditions can be satisfied by using 1D grating and 1D surface waves, as long as the incidence wave does not contain a wave vector component perpendicular to the micro-flow direction. Again, the use of such a 1D grating structure having a defined period serves to enhance the transmission received through nanoholes 1200 while providing increased resolution.

Scheme 3

Figure 15:
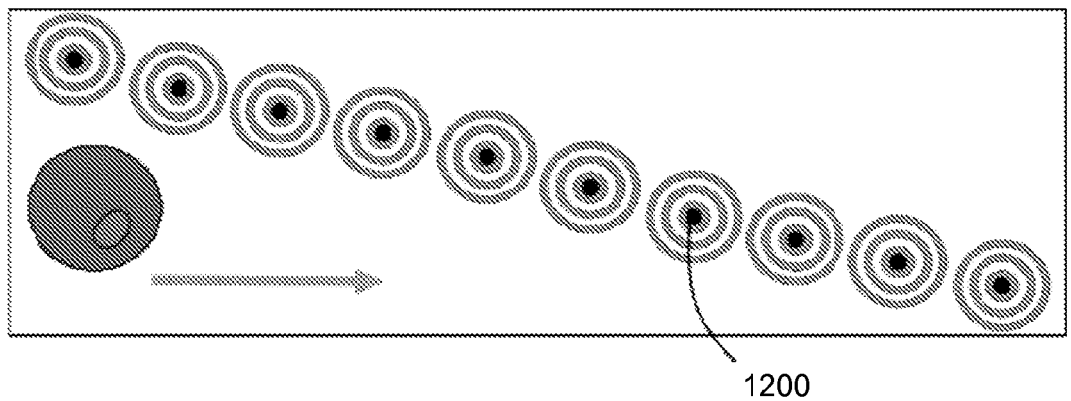
FIG. 15 illustrates the use of a corrugated ring structure in accordance with one or more embodiments of the invention.

It has been shown that the anomalous transmission phenomenon can also be observed in a ring structure with a through-hole at the center of the concentric rings [MICRO11]. Such a configuration may also be used in dark-field OFM and the physics behind the destructive interference is similar to the two previous cases. FIG. 15 illustrates the use of such a ring structure in accordance with one or more embodiments of the invention. Thus, as illustrated in FIG. 15, concentric circle corrugations are used to enhance the transmission through nanoholes 1200.

Scheme 4

Knowledge of the length of nano-particles can be an invaluable resource. For example, numerous applications of microfluidics based nano-rulers has been useful in biological research, such as measuring the length of the extended DNA molecules ([MICRO13] and [MICRO14]) and the distance between two fluorescent cells within a microorganism.

Figure 16:
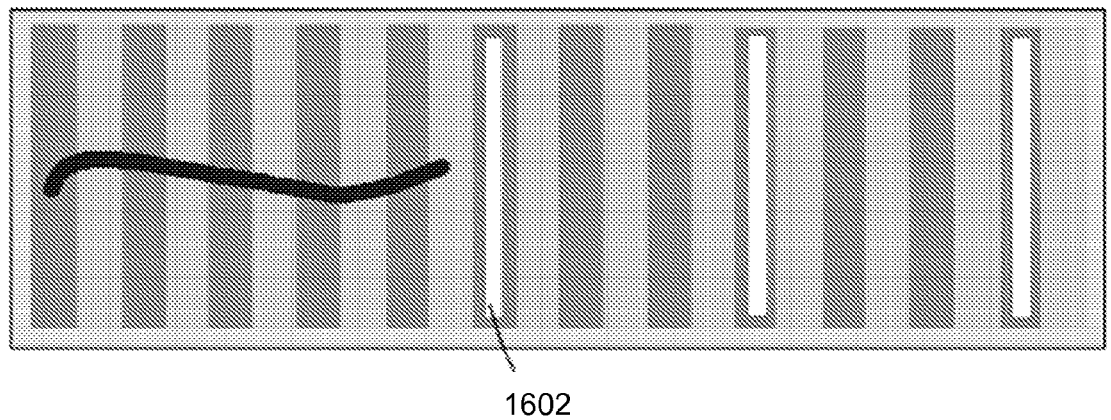
FIG. 16 illustrates the use of a microfluidic based nanoruler in accordance with one or more embodiments of the invention.

Dark-field OFM can be readily modified for this type of application. It can be applied as a high-resolution ruler or particle sorter in microfluidic settings. FIG. 16 illustrates the use of a microfluidic based nano-ruler in accordance with one or more embodiments of the invention. As illustrated, the size of the slit 1602 can affect the resolution similar to the size of a nanohole 1200. In this regard, the smaller the slit or nanohole, the higher the resolution. However, as the size of the slit 1200 decreases, the transmission quality decreases. Accordingly, what is needed is the capability to maintain a high resolution (i.e., via a small slit 1602) while enhancing the transmission. A corrugation pattern such as that illustrated in FIG. 16 serves to enhance the transmission in a desirable manner. In FIG. 16, a corrugation pattern similar to that used in schema 2 (i.e., FIG. 14) is used.

Scheme 5

Figure 17:
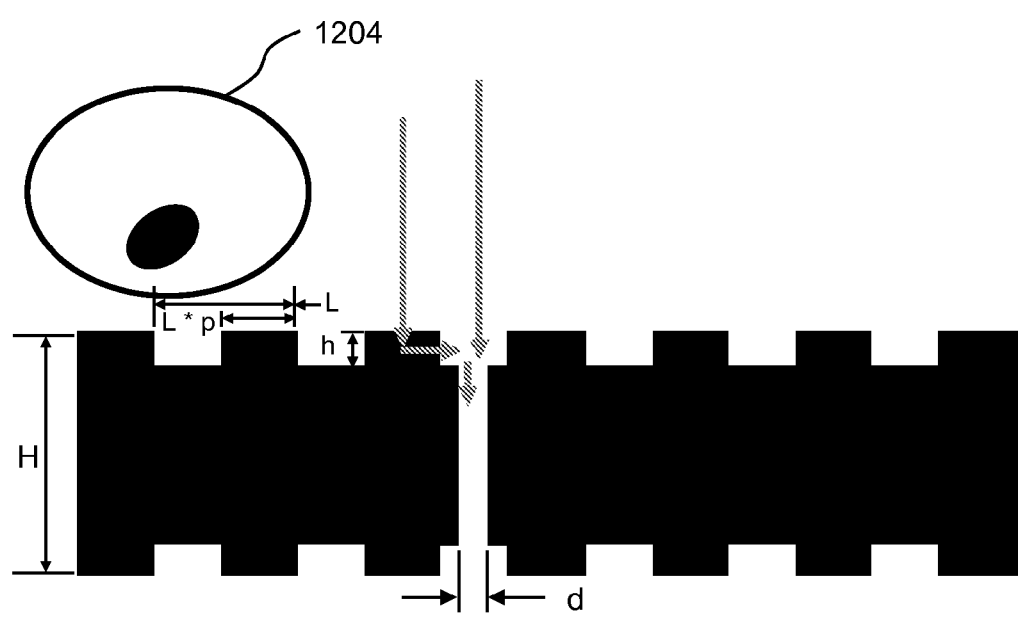
FIG. 17 illustrates a periodical configuration fabricated on the top and bottom of a surface containing apertures in accordance with one or more embodiments of the invention.

In order to facilitate the coupling between surface plasmon waves at the top surface and the bottom surface, periodical corrugation can be made on both the bottom and top surfaces as shown in FIG. 17. The parameters used in the design, e.g.

h (height of the corrugation), L (period), d (diameter of nanohole), H (height of the metallic film) and p (duty cycle) denote the same features as those in FIG. 12. Making surface corrugation on the bottom surface results in a more directed transmitted light beam [MICRO11], which can be much more efficiently collected by an objective lens or a CMOS sensor. The type of device may be made as a free-standing structure, and the fabrication procedure has been demonstrated [MICRO11].

Bright Field OFM and Enhancement of Optical Transmission Through a Subwavelength Hole Surface plasmons are considered as collective electron excitations, which are characterized by intensive electromagnetic fields confined on the surface of highly conductive metal (e.g. Al, Ag, Au). The interaction of surface plasmons with probe light is able to enhance the transmission of subwavelength holes [MICRO1][MICRO11].

In the visible spectral range, surface plasmon waves have a larger momentum (wave number) than propagating light, so the plasmon waves do not couple to each other efficiently without fine local structures, usually nanostructures. Careful selection of the parameters in FIGS. 12 and 17 can result in strong coupling between light and surface plasmons, which enhances the transmission through nanoholes. The well accepted momentum matching formula is:

$$K_{sp} = K_0 + mG_x + lG_y \quad (1)$$

$K_{sp}$ is the wave vector of surface plasmon wave $$K_{sp}(\omega) = \frac{\omega}{c}\sqrt{\frac{\varepsilon_m(\omega)\varepsilon_s}{\varepsilon_m(\omega)+\varepsilon_s}} \quad (2)$$

, $\varepsilon_s$: dielectic medium, $\varepsilon_m$: metal $K_0$ is the wave vector of light in the top dielectric medium.

$$G_x = \frac{2\pi}{L_x}$$

is the $1^{st}$ order vector in the x direction of the reciprocal lattice of the periodical corrugation.

$$G_y = \frac{2\pi}{L_y}$$

is the $1^{st}$ order vector in the y direction of the reciprocal lattice of the periodical corrugation.

Note that the above formulas are only approximations for satisfying the SP-light resonance condition; the dispersion relation of $K_{sp}$ is modified when the periodical surface corrugation is introduced. However this momentum matching formula works successfully when the corrugation is sufficiently shallow so that the impact on smooth-surface $K_{sp}$ is weak.

Under normal conditions, this light transmission is extremely weak and requires the use of photomultiplier tube (PMT) or avalanche photodiode (APD) detectors for detection. In other words, it precludes the use of a cheap optical detector such as a complimentary metal-oxide-semiconductor (CMOS) sensor as a detector option. Bright field OFM assisted by surface plasmon aims at making use of the enhancement in optical transmission through nanoholes (e.g. 100 nm in diameter) to significantly boost a weak transmission, and thereby enable the use of CMOS sensors.

The configurations of bright-field OFM are similar to those of dark-field OFM (see FIGS. 12-17), with only changes in the selection of design parameters (e.g. L, p, d). The resonance condition of surface plasmon (SP)-light coupling is very sensitive to the surrounding medium. Accordingly, the existence of a biological sample breaks down the resonance condition and will immediately change the transmission though the nanohole.

Bright field OFM assisted by surface plasmon is considered very important for high resolution fluorescence imaging. Fluorescence signals carry rich and important biological information. Unfortunately, fluorescence is usually weak and efficient detection is accomplished by using a bulky detector, such as an APD or a PMT with a long integration time. With the SP-light coupling condition tuned for a specific fluorescence band, the fluorescence signal will be able to efficiently couple into the nanohole and be transmitted with an enhanced power.

In accordance with one or more embodiments of the invention, the interaction between surface plasmon and probing light is facilitated by the introduction of surface corrugations. The interference can be fined tuned for destructive interference condition in dark-field OFM as well as for constructive interference condition in bright field OFM.

Consider the case where an isolated nanohole is drilled on a smooth metal surface. The propagation wave scattered by the sample when reaching the subwavelength hole will not be transmitted efficiently. Only the near field component of the scattered light can efficiently couple with the surface plasmon wave. Careful design of nanostructures surrounding the nanohole not only enhances the interaction between the surface plasmon and the scattered light, but also facilitates the coupling of the surface plasmon wave on the top surface with that on the bottom surface. In other words, the localized (near field) information of the sample can be more effectively coupled by the detector underneath the nanohole.

The resolution of the nanohole based optical imaging may be compromised to some extent due to the SP-light coupling. This coupling is quite different from the case where an isolated nanohole is used in OFM. Light beaming effect (its physics is approximately explained by equation 1 above) provides a better selection of the direction of probing light in both the far field and near field.

In addition, it may be noted that the interference between the surface plasmon wave and the directly transmitted wave can also be arranged to be at other relative phases. In the situation where the two waves are arranged to be 90° out of phase, any change in the relative phase of the two waves will be maximally translated into transmission signal change.

Figure 18:
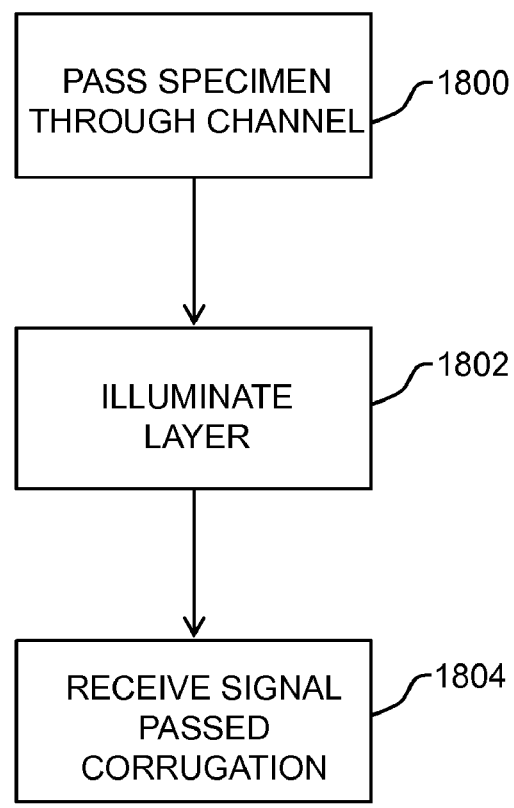
FIG. 18 is a flow chart illustrating the logical flow for enhancing a transmission signal in a surface plasmon assisted optofluidic microscope in accordance with one or more embodiments of the invention

FIG. 18 is a flow chart illustrating the logical flow for enhancing a transmission signal in a surface plasmon assisted optofluidic microscope in accordance with one or more embodiments of the invention. At step 1800, a specimen is passed through a body comprising a fluid channel having a layer as a surface.

At step 1802, the layer is illuminated. As described above, the layer has at least one aperture that is configured to receive the illumination from an illumination source. Further, a surface plasmon wave propagates along the surface (e.g., the surface/layer is a metallic film).

At step 1804, a signal that is based on the illumination passing through the aperture is received on a photodetector. In addition, a corrugation is fabricated onto the surface and parameters of the corrugation optimize the signal received on the photodetector. Thus, the signal that is received passes across the corrugation thereby enhancing the transmission while maintaining a high resolution. Since the signal is based on the corrugation parameters, such parameters may be tuned to enhance destructive interference in a dark field microscope or may be tuned to enhance constructive interference in a bright field microscope.

The corrugation/corrugation parameters (e.g., grating) may be fabricated in accordance with various different schema. In one schema, multiple apertures are established in a slanted pattern on the corrugation having a rectangular lattice pattern. In a second schema, multiple apertures are established in slanted pattern on the corrugation having a 1D grating structure pattern. In a third schema, a slanted pattern of multiple apertures are established each in a center of the corrugation defined by concentric rings. In fourth schema, the length of a nanoparticle may be measured based on the signal received on the photodetector (i.e., the corrugation and apertures/slits provide a nanoruler structure). In a fifth schema, the corrugation is fabricated onto both a top and bottom of the surface containing the apertures.

The different schemas described herein may be used in combination with the DIC microscopes and phase-beam profilers described above. In this regard, the layer used in the DIC microscopes may also have corrugated surfaces that provide a surface plasmon-assisted optofluidic microscope.

CONCLUSION

This concludes the description of the preferred embodiment of the invention. The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

REFERENCES

[DIC1] Differential Interference Contrast (DIC), Murphy, Schwartz, Salmon, Spring, Parry-Hill, Sutter, and Davidson, 2007, available from Nikon MicroscopyU at http://www.microscopyu.com/articles/dic/dicindex.html;

[DIC2] Cui, X., Heng, X., Erickson, D., Psaltis, D., Yang, C. "Portable optical microscope-on-a-chip" Photonics West, San Jose, Calif., January 2006;

[DIC3] Introduction to Confocal Microscopy, Dunn, Wang, Paddock, Hzen, DeVries, Pawley, Parry-Hill, Fellers, and Davidson, 2007, available from MicroscopyU at http://www.microscopyu.com/articles/confocal/;

[DIC4] M. R. Arnison, K. G. Larkin, C. J. R. Sheppard, N. I. Smith, and C. J. Cogswell, "Linear phase imaging using differential interference contrast microscopy", Journal of Microscopy, Vol. 214, Pt. I April 2004, pp. 7-12;

[DIC5] Xiquan Cui, Xin Heng, Jigang Wu, Zahid Yaqoob, Axel Scherer, Demetri Psaltis, and Changhuei Yang, "Slanted hole array beam profiler (SHArP)—a high-resolution portable beam profiler based on a linear aperture array", Optics Letters, Vol. 21, No. 21, Nov. 1, 2006. pp 3161-3163;

[MICRO1] Lezec, H. J. and T. Thio, *Diffracted evanescent wave model for enhanced and suppressed optical transmission through subwavelength hole arrays.* Optics Express, 2004. 12(16): p. 3629-3651;

[MICRO2] Fu, A. Y., et al., *A microfabricated fluorescence-activated cell sorter.* Nature Biotechnology, 1999. 17(11): p. 1109-1111;

[MICRO3] Tai, Y. C., et al., *Integrated micro/nano fluidics for mass-spectrometry protein analysis.* International Journal of Nonlinear Sciences and Numerical Simulation, 2002. 3(3-4): p. 739-741;

[MICRO4] Tokeshi, M., et al., *Chemical processing on microchips for analysis, synthesis, and bioassay.* Electrophoresis, 2003. 24(21): p. 3583-3594;

[MICRO5] Doyle, P. S., et al., *Self-assembled magnetic matrices for DNA separation chips.* Science, 2002. 295 (5563): p. 2237-2237;

[MICRO6] Trau, D., et al., *Genotyping on a complementary metal oxide semiconductor silicon polymerase chain reaction chip with integrated DNA microarray.* Analytical Chemistry, 2002. 74(13): p. 3168-3173;

[MICRO7] Liu, S. R., *A microfabricated hybrid device for DNA sequencing.* Electrophoresis, 2003. 24(21): p. 3755-3761;

[MICRO8] Heng, X., et al., *Optofluidic microscope, a miniature microscope on a chip.* 9th International Conference on Miniaturized Systems for Chemistry and Life Sciences (µTAS), 2005;

[MICRO9] Bouwkamp, C. J., *Diffraction theory.* Reports on Progress in Physics XVIII, 1954: p. 35;

[MICRO10] de Abajo, F., *Light transmission through a single cylindrical hole in a metallic film.* Optics Express, 2002. 10(25): p. 1475-1484;

[MICRO11] Lezec, H. J., et al., *Beaming light from a subwavelength aperture.* Science, 2002. 297(5582): p. 820-822;

[MICRO12] Ebbesen, T. W., et al., *Extraordinary optical transmission through sub-wavelength hole arrays.* Nature, 1998. 391(6668): p. 667-669;

[MICRO13] Tegenfeldt, J. O., et al., *Near-field scanner for moving molecules.* Physical review letters, 2001. 86(7): p. 1378-1381; and

[MICRO14] Tegenfeldt, J. O., et al., *Micro- and nanofluidics for DNA analysis.* Analytical and Bioanalytical Chemistry, 2004. 378(7): p. 1678-1692.

What is claimed is:

1. A surface wave assisted device comprising:
a layer having an aperture and a first surface, wherein a surface wave propagates along the first surface; and
a corrugation in the first surface, the corrugation configured to modify the surface wave to increase destructive interference to adjust an amount of illumination being transmitted through the aperture.

2. The surface wave assisted device of claim 1, wherein the first surface is configured to receive illumination from an illumination source.

3. The surface wave assisted device of claim 2, wherein the layer further comprises a second surface opposing the first surface, the second surface having another corrugation configured to modify another surface wave propagating along the second surface to adjust illumination transmitted from the aperture.

4. The surface wave assisted device of claim 1, wherein the corrugation is further configured to modify the surface wave to increase constructive interference to adjust the amount of illumination being transmitted through the aperture in the presence of an optical discontinuity at the aperture.

5. The surface wave assisted device of claim 1, wherein the corrugation is configured to modify the surface wave to increase destructive interference of illumination associated with a first wavelength and to increase constructive interference of illumination associated with a second wavelength.

6. The surface wave assisted device of claim 1, further comprising a detector configured to generate a signal associated with illumination transmitted through the aperture.

7. The surface wave assisted device of claim 6, wherein the detector is a photodetector.

8. The surface wave assisted device of claim 1, wherein the corrugation comprises one or more grooves.

9. The surface wave assisted device of claim 8, wherein the one or more grooves form a lattice structure.

10. The surface wave assisted device of claim 8, wherein the one or more grooves form of a 1D grating structure.

11. The surface wave assisted device of claim 8, wherein each groove is a ring structure around the aperture.

12. A surface wave assisted dark field device comprising:
   a layer having an aperture and a first surface, wherein a surface wave propagates along the first surface; and
   a corrugation in the first surface, the corrugation configured to provide a dark field by modifying the surface wave to increase destructive interference, wherein in the absence of an optical discontinuity at the aperture the modified surface wave destructively interferes with illumination being transmitted through the aperture.

13. The surface wave assisted dark field device of claim 12, wherein the corrugation is further configured to provide the dark field by modifying the surface wave to increase constructive interference, wherein in the presence of the optical discontinuity at the aperture the modified surface wave constructively interferes with illumination being transmitted through the aperture.

14. The surface wave assisted dark field device of claim 12, further comprising a detector configured to generate a signal associated with illumination transmitted through the aperture.

15. The surface wave assisted dark field device of claim 12, wherein the surface wave assisted dark field device is a dark field microscope.

16. The surface wave assisted dark field device of claim 12, wherein the first surface is configured to receive illumination from an illumination source.

17. The surface wave assisted dark field device of claim 16, wherein the layer further comprises a second surface opposing the first surface, the second surface having another corrugation configured to modify another surface wave propagating along the second surface to adjust illumination transmitted from the aperture.

18. A surface wave assisted optofluidic device comprising:
   a body comprising a fluid channel having a layer with at least one aperture and a first surface, wherein a surface wave propagates along the first surface; and
   a corrugation in the first surface, the corrugation configured to modify the surface wave to adjust an amount of illumination being transmitted through the at least one aperture, wherein the corrugation is configured to modify the surface wave to increase destructive interference.

19. The surface wave assisted optofluidic device of claim 18, wherein the corrugation is further configured to modify the surface wave to increase constructive interference.

20. The surface wave assisted optofluidic device of claim 18, wherein the corrugation is configured to modify the surface wave to increase destructive interference of illumination associated with a first wavelength and to increase constructive interference of illumination associated with a second wavelength.

21. The surface wave assisted optofluidic device of claim 18, further comprising a detector configured to generate a signal associated with illumination transmitted through the at least one aperture.

22. The surface wave assisted optofluidic device of claim 18, wherein the at least one aperture forms of an array diagonally extending from a first lateral side to a second lateral side of the fluid channel.

23. The surface wave assisted optofluidic device of claim 18, wherein the at least one aperture comprises a slit extending from a first lateral side to a second lateral side of the fluid channel.

24. The surface wave assisted optofluidic device of claim 18, wherein the first surface is configured to receive illumination from an illumination source.

25. The surface wave assisted device of claim 24, wherein the layer further comprises a second surface opposing the first surface, the second surface having another corrugation configured to modify another surface wave propagating along the second surface to adjust illumination transmitted from the aperture.

26. A method of adjusting illumination transmitted through at least one aperture in a surface wave assisted optofluidic device, the method comprising:
   passing a specimen through a fluid channel in a body of the surface wave assisted optofluidic device, the fluid channel having a layer with the at least one aperture, wherein a surface wave propagates along a surface of the layer;
   modifying the surface wave by a corrugation in the surface; and
   adjusting the illumination being transmitted through the at least one aperture based on destructive interference associated with the modified surface wave.

27. The method of claim 26, further comprising measuring a signal by a detector based on the illumination transmitted through the at least one aperture.

28. The method of claim 26, further comprising measuring a length of the specimen based on the illumination transmitted through the at least one aperture.

29. The method of claim 26, further comprising in the presence of an optical discontinuity, increasing the illumination transmitted through the at least one aperture based on constructive interference associated with the modified surface wave.

30. The method of claim 26, wherein the corrugation is configured to modify the surface wave to increase destructive interference of illumination associated with a first wavelength and to increase constructive interference of illumination associated with a second wavelength.

* * * * *

UNITED STATES PATENT AND TRADEMARK OFFICE
CERTIFICATE OF CORRECTION

PATENT NO. : 8,411,282 B2  
APPLICATION NO. : 13/157245  
DATED : April 2, 2013  
INVENTOR(S) : Xiquan Cui et al.

Page 1 of 1

It is certified that error appears in the above-identified patent and that said Letters Patent is hereby corrected as shown below:

Title Page;

[75] Inventor Xiquan Cui residence address change from "Pasadena, CA" to San Jose, CA.

Signed and Sealed this  
Fourth Day of June, 2013

Teresa Stanek Rea  
*Acting Director of the United States Patent and Trademark Office*